United States Patent
Zvuloni et al.

(10) Patent No.: US 9,392,960 B2
(45) Date of Patent: Jul. 19, 2016

(54) FOCUSED PROSTATE CANCER TREATMENT SYSTEM AND METHOD

(75) Inventors: Roni Zvuloni, Haifa (IL); Shaike Schatzberger, Haifa (IL)

(73) Assignee: UC-CARE LTD., Yokneam (IL)

(*) Notice: Subject to any disclaimer, the term of this patent is extended or adjusted under 35 U.S.C. 154(b) by 484 days.

(21) Appl. No.: 13/805,535

(22) PCT Filed: Jun. 23, 2011

(86) PCT No.: PCT/IL2011/000507
§ 371 (c)(1),
(2), (4) Date: Dec. 19, 2012

(87) PCT Pub. No.: WO2011/161684
PCT Pub. Date: Dec. 29, 2011

(65) Prior Publication Data
US 2013/0090554 A1    Apr. 11, 2013

Related U.S. Application Data

(60) Provisional application No. 61/358,034, filed on Jun. 24, 2010.

(51) Int. Cl.
| | |
|---|---|
| A61B 5/06 | (2006.01) |
| A61B 10/02 | (2006.01) |
| A61B 8/12 | (2006.01) |
| A61B 17/00 | (2006.01) |
| A61B 18/00 | (2006.01) |

(52) U.S. Cl.
CPC . *A61B 5/061* (2013.01); *A61B 8/12* (2013.01); *A61B 10/0241* (2013.01); *A61B 2017/00274* (2013.01); *A61B 2018/00547* (2013.01); *A61B 2034/2072* (2016.02)

(58) Field of Classification Search
CPC ...... A61B 5/061; A61B 8/12; A61B 10/0241; A61B 19/56; A61B 2017/00274; A61B 2018/00547; A61B 2019/5251; A61B 2019/5272; A61B 2019/5276; A61B 2019/505
See application file for complete search history.

(56) References Cited

U.S. PATENT DOCUMENTS

| | | | |
|---|---|---|---|
| 7,670,333 | B2 | 3/2010 | Schatzberger |
| 2009/0048515 | A1 | 2/2009 | Suri |

FOREIGN PATENT DOCUMENTS

| | | | | |
|---|---|---|---|---|
| EP | 0459535 | | 3/2008 | |
| WO | 2004/002319 | | 1/2004 | |
| WO | WO2008/063249 | * | 5/2008 | ............... A61B 8/00 |
| WO | 2009/071766 | | 6/2009 | |

* cited by examiner

*Primary Examiner* — Bo J Peng
(74) *Attorney, Agent, or Firm* — Dorsey & Whitney LLP

(57) ABSTRACT

Systems and methods for locating lesions in a prostate or other organ during a first intervention session, and for using that lesion location information during a second intervention session are presented. A module for detecting and reporting the position of a prostate in real time is disclosed. The module comprises a sensor which detects and electronic signal. An image registration system for mapping first-session 3D model information to a second-session 3D model is also presented, as is a prostate modeling facilitation tool which comprises a set of predefined 3D models of the prostate.

16 Claims, 25 Drawing Sheets

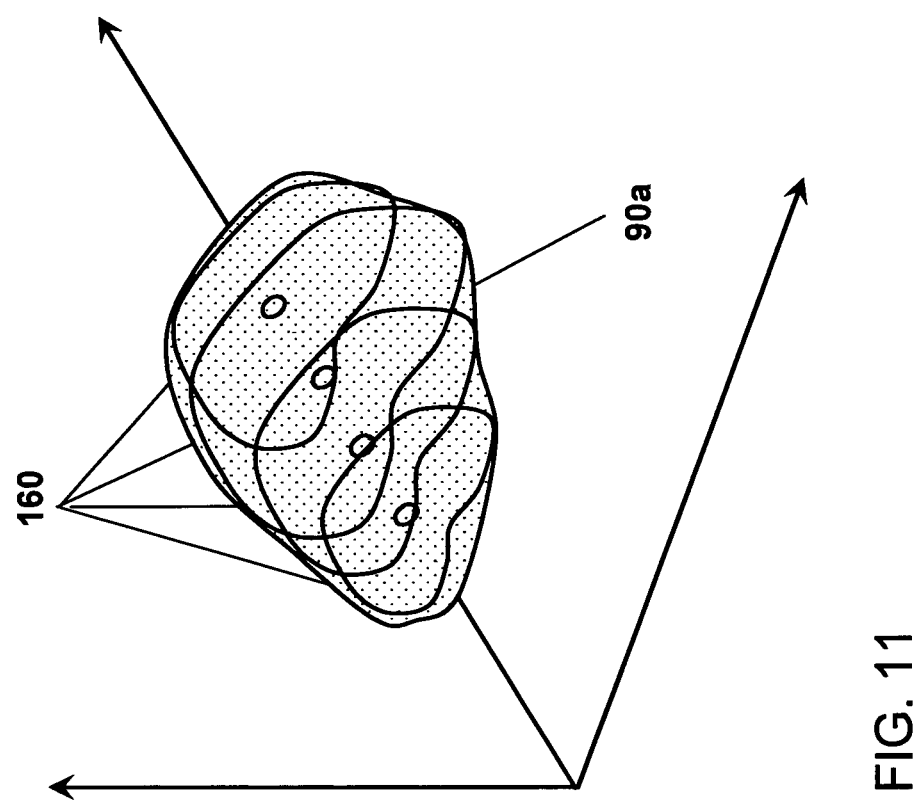

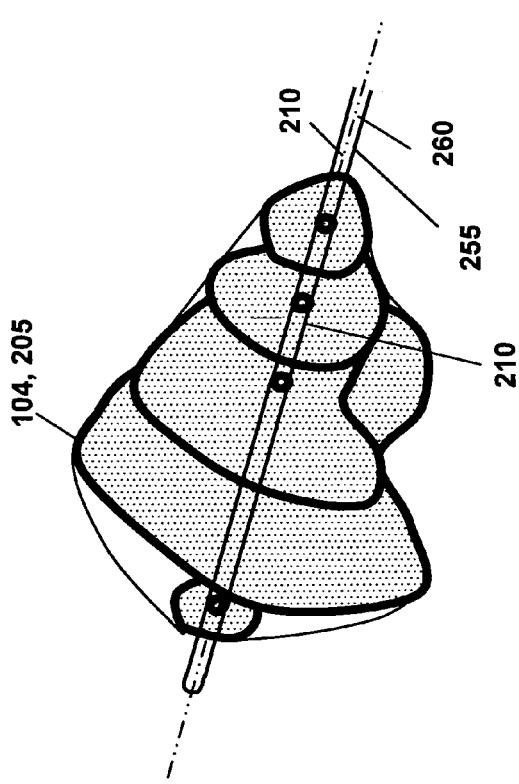
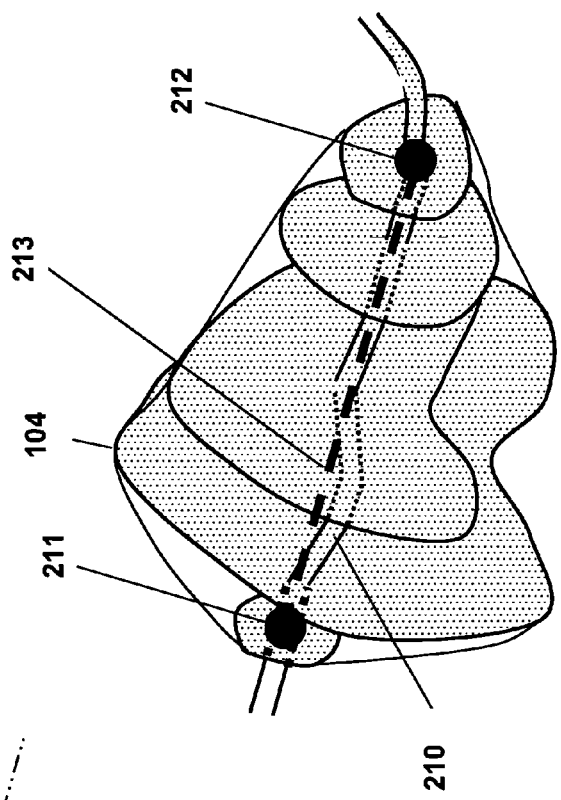
FIG. 16A
FIG. 16B

FOCUSED PROSTATE CANCER TREATMENT SYSTEM AND METHOD

RELATED APPLICATIONS

This Application is the U.S. National Stage of International Application No. PCT/IL2011/000507, filed Jun. 23, 2011, which claims priority from U.S. Provisional Application No. 61/358,034 for "Focused Prostate Cancer Treatment System and Method" filed Jun. 24, 2010. The contents of the above-mentioned application are incorporated herein by reference.

FIELD OF THE INVENTION

The present invention, in some embodiments thereof, relates to devices and methods for diagnosis and/or ablative therapy of a selected portion of an organ. More particularly, the present invention relates to systems and methods for detecting, diagnosing, and selectively treating diseased portions of an organ such as a prostate, while avoiding unnecessary destruction of healthy tissues in within and around the organ during such treatment.

BACKGROUND OF THE INVENTION

The present invention relates to methods and apparatus for delivering a medical instrument to a diagnostic and/or treatment site within the body of a patient. More particularly, the present invention simplifies diagnosis and treatment of a variety of ailments by enabling accurate placement of surgical and/or diagnostic tools in areas not directly visible to a surgeon during a medical procedure.

Surgical treatment of tumors and other conditions usually involve a first set of procedures undertaken for diagnostic purposes, followed, often at a different place and on a different day, by a second set of procedures for more detailed diagnosis and/or for treatment of a condition detected by the first set of procedures.

Location information transfer between diagnostic phase procedures and treatment phase procedures involves intrinsic difficulties: an organ inspected at a first time in a first position under an imaging modality such as an imaging probe (e.g. an ultrasound probe) may look completely different when inspected during further diagnostics or treatment, perhaps days later, with patient in a more or less different position, the organ subject to somewhat different weights and pressures, the imaging equipment being somewhat differently positioned, etc. According to methods of prior art it is standard practice to re-do various diagnostic procedures (e.g. diagnostic imaging) on the day of treatment (e.g. ablative surgery) rather than attempting to use previously gathered location information to guide a surgical procedure, despite disadvantages of inefficiency through repetition of time-consuming procedures, additional exposures to ionizing radiation, exposure to radioactive elements, and various other inconveniences. Some physicians also base treatment on previously gathered location information adjusted to the changed situation of a later treatment session merely according to the physician's impression based only on limited information such as printed records of 2D ultrasound images.

When repetition of diagnostic procedures is not convenient or not practical, surgeons lacking means to relate diagnostic-phase information to a real-time treatment context usually choose to "err on the side of caution" and to ablate healthy tissues along with pathological tissues, because of lack of an efficient means of distinguishing between the two at the time of treatment.

Such has been clinical practice, for example, in prostate surgery. According to prior art methods, once a cancer of the prostate is diagnosed, standard clinical procedure has been to ablate all or most of the prostate, thereby assuring that all the cancer has been destroyed. It has been suggested that one reason for this standard clinical practice has been that detection and localization of specific malignant sites within a prostate is difficult to do: once a problematic site has been identified during a first (diagnostic) procedure, the generally soft and flexible nature of prostate tissue is such as to render it difficult for a surgeon to accurately return to that detected and diagnosed site during a second (ablative) procedure.

The percentage of men who will develop prostate cancer in their lifetime is extremely high. Once a prostate cancer is detected, it is common clinical practice to ablate most or all of the prostate, in order to be sure that all malignant portions of the prostate have been destroyed. Yet, there are several known disadvantages to general ablation of most or all of a prostate. Prostate surgery not infrequently results in damage to the neurovascular bundle, to the urethra and the urethral sphincters, to the rectum, and to various other healthy and potentially important tissues in the neighborhood of the prostate. Damage to such tissues can lead to incontinence, to impotence, and to a variety of other complications ranging from the merely uncomfortable, through those which retard recovery, to those which comprise serious long-term or permanent deleterious effects on patients' length of life and quality of life.

It is noted that there exists a diagnostic procedure for detecting prostate cancer known in the art as "saturation biopsy", comprising taking numerous tissue samples from throughout the prostate. Perhaps because prior art clinical practice generally calls for ablation of most or all of the prostate once a cancer has been detected, saturation biopsy as currently practiced does not comprise maintaining accurate records of the positions of source sites of each individual tissue sample, and indeed generally involves mixing or combining of tissues taken from several sites prior to diagnostic pathological examination of the tissues.

Saturation biopsy performed through the perineum requires anesthesia, either general anesthesia or a periprostatic block. Therefore more than about 95% of the prostate biopsies are performed via the rectum by "blind" free-hand insertion of the biopsy needle via a needle guide mounted on a TRUS transducer, or via a cannula passing through a TRUS transducer. Though the procedure may be performed under ultrasound guidance, the physician has only rough and estimated information as to the location from which each biopsy has been taken. Records for the biopsy locations by means of TRUS records under these circumstances are not accurate and are largely useless, and in practice are not used in subsequent procedures

SUMMARY OF THE INVENTION

The present invention, in some embodiments thereof, relates to methods and apparatus for delivering a medical instrument to a diagnostic and/or treatment site within the body of a patient. More particularly, the present invention simplifies diagnosis and treatment of a variety of ailments by enabling accurate placement of surgical and/or diagnostic tools in areas not directly visible to a surgeon during a medical procedure.

By providing apparatus and methods for using information gleaned from a first (e.g. diagnostic) set of procedures during a second (e.g. therapeutic) set of procedures, some embodiments of the invention can eliminate the need to repeat some diagnostic acts during treatment phase, and can eliminate the necessity for therapies wherein major portions of healthy tissue portions are unnecessarily destroyed along with pathological tissue. Some embodiments enable to utilization of location-specific diagnostic information gleaned during diagnostic phase activity to specifically guide and direct treatment activity to specific locations diagnosed as pathological.

Diagnosis and treatment of conditions of the prostate is particularly suited to use of embodiments of the invention described herein, however exemplary discussions of prostate surgery herein should not be taken as limiting. Embodiments of the invention can be applied to diagnosis and/or treatment of a variety of ailments in a variety of organs. However, although the invention is not limited to prostate surgery, examples from the field of prostate surgery will be discussed in the following description of exemplary embodiments. Descriptions herein relating to the prostate should be understood to relate to the prostate in exemplary fashion, and should be considered as relevant to any organ, for example to the kidney, liver, uterus, and lung.

It is noted that references to "diagnostic phase" activity and "treatment phase activity" as used herein are not intended to be limiting. These phrases are convenient for simplicity of exposition, since a prostate treatment cycle typically involves a diagnostic set of procedures performed at a first time and place followed by a treatment set of procedures performed at a second time and place. However it is to be understood that embodiments of the invention are relevant to many multi-phase activities, including multi-phase diagnostic procedures and/or multi-phase treatment procedures, and/or repeated exploratory and/or interventionary activity of any sort. The terms "first phase" activity and "diagnostic phase" activity should be understood to include any procedures of a first set of procedures, and the terms "second phase" activity and "treatment phase" activity should be understood to include any procedures of a second set of procedures practiced at a time later than that of the first phase procedures.

It is noted that although various embodiment features are presented herein in the context of particular embodiments, it is contemplated that features described in the context of particular embodiments may be combined in any combination to produce systems and methods combining features which were described separately (e.g. in different figures or in different portions of the disclosure). Embodiments of the present invention are deemed to include all such combinations of features described herein and/or presented in any of the figures.

In some embodiments, real-time or near real-time imaging modalities and/or 3D spatial tracking systems and/or 3D modeling of body organs are used to characterize intervention sites at known spatial locations during a first set of procedures, and then a 3D spatial tracking system, a 3D model, and alignment (registration) tools are used to enable guiding a second set of procedures during a second surgical intervention based on first-procedure characterizations of intervention sites, optionally at a time, place, set-up, and patient position different from those of the first intervention. Some embodiments also comprise tools for compensating for patient movements during procedures. Some embodiments are useful in, for example, interventional cardiology, interventional gastrology, interventional urology, interventional gynecology, endoscopy and laparoscopy, as well as in other medical disciplines.

Some embodiments comprise sampling tissues at a plurality of locations during a first phase of activity, analyzing those tissues to select those where treatment is required, optionally repeating such diagnostic activity as needed, then directing introduction of surgical tools or surgical energies to sites so selected during second phase activity. Use of embodiments here presented may enhance speed, efficiency, accuracy, and simplicity of some treatment procedures.

Embodiments of the present invention provide apparatus and methods for inserting diagnostic tools such as biopsy needles into a prostate or other organ at known positions, for localizing (determining and recording locations of) tissue sample sources within the organ, diagnosing individual neighborhoods within a prostate by diagnostic analysis of the individually localized tissue samples, selecting sites for treatment according to the results of that analysis, and guiding treatment towards those individually selected sites. Information gleaned during first (e.g. diagnostic) phase activity is made available during second (e.g. treatment) phase activity, and enables to treat conditions such as prostate cancer while avoiding destruction to prostate regions deemed to be free of cancer.

Some embodiments localize tissue samples with respect to one or more images, and/or with respect to a three-dimensional model, and/or with respect to a reproducible coordinate system, and/or with respect to anatomical landmarks and/or with respect to one or more fiduciary (physical) markers inserted in the organ, and/or with respect to one or more sensors inserted in the organ, and/or with respect to one or more sensors inserted in a natural body conduit, and/or with respect to sensors around the body capable of detecting the organ spatial position, and/or with respect to an organ-constraining device such as a prostatic urethral straightener used to constrain the position and/or the form of a flexible organ.

Some embodiments comprise manual and/or automatic information-guided insertion of insertable diagnostic tools, and/or insertable ablation tools or other treatment tools to individual body sites diagnosed as requiring treatment, and/or focusing of imaging tools for enhanced diagnostics of such sites, and/or focusing of externally supplied energies such as HIFU (High Intensity Focused Ultrasound) towards such sites.

Using these methods, a 'shotgun' tissue sampling approach may be accurately coupled with a specifically directed treatment approach: multiple biopsy samples may be taken throughout a prostate or other organ, each sample's position in the organ being accurately recorded. Each sample may then be diagnostically analyzed, and treatment may then be directed to only those sites and site neighborhoods found to contain pathological tissues. Similarly, sampling locations information recorded during first-phase biopsy sampling can be used to direct second-phase additional biopsy sampling to tissue areas that were not previously examined, and/or to tissues proximate to areas diagnosed as problematic. Such localized and focused treatment facilitates protection of healthy non-prostate structures near the prostate, thereby enhancing recovery of prostate surgery patients and reducing some of the serious health risks known to accompany prostate surgery when practiced according to methods of prior art.

More generally stated, embodiments described herein comprise methods and systems for extracting tissue samples from a plurality of loci within a body, recording a tissue source position for each tissue sample, analyzing the tissue samples to identify tissue neighborhoods requiring ablative treatment, and then guiding treatment tools or treatment energies to each neighborhood so identified.

In some embodiments a first three-dimensional model is created, based on first images taken during first phase activity. A second three-dimensional model is also created, based on second images taken during second phase activity. During the second phase, first and second phase images and/or first and second phase models are mapped to each other, so information from the first-phase intervention is available during second-phase intervention, and can be understood in terms of the second-phase (e.g. real-time) images and/or 3D model. (The terms "alignment" and "registration" of first and second 3D models and/or first and second images provided by imaging modalities should be understood to include reference to construction and/or use of such a mapping.

In some embodiments mapping from a first-phase 3D model's virtual space to a second-phase 3D model's virtual space is facilitated by (user-assisted or algorithmic) comparison of each model's locating of recognizable physiological landmarks within the body. Some examples:

The prostatic urethra is a landmark which can be found in both first and second phase ultrasound images of a prostate.

The urethra entrance to the bladder neck and the prostate-urethra end at the apex are easily found and identified.

The seminal vesicles near the prostate can be identified and used as landmarks.

The prostate gland borders may also be used as landmarks.

These and similar landmarks can be recognized using image analysis software, or alternatively can be marked by a user on a real-time or other image presented on a computer screen. Spatial locations of these landmarks, as reported by the imaging software and/or 3D tracking apparatus or position-detection sensors can then be recorded.

Fiduciary markers (for example Civco Inc., Fiducial Marker Kit) may also be used to provide visible landmarks common to first and second images and models. (Fiducial markers are also called "fiduciary markers" and "physical markers" herein.) Optionally, spatial positions of imaging tools and/or other parameters thereof may also be recorded to provide information useful in relating apparent position of objects on an image with actual position of those objects in three-dimensional real space.

In some embodiments, organs are positionally constrained in repeatable ways, thereby reducing differences between first and second images of a same organ between diagnostic phase and treatment phase imaging. By means of such constraint, change may be reduced in amount and limited to fewer variables or to fewer dimensions, thereby facilitating automated comparisons between first and second images and/or human comparisons of first and second images undertaken by the eye of a surgeon, and further facilitating mappings between first and second three-dimensional models and/or graphic manipulations such as combining data from first and second images to produce a combined image for display.

For example, in some embodiments a urethral straightening device is used as an organ-constraining device. The urethral straightening device is insertable into a prostatic urethra during the diagnostic phase and again inserted into the prostatic urethra during a treatment phase. As a result, differences in shape of that organ between the taking of first-phase images and the taking of second-phase images are substantially reduced. Moreover, since the position of the urethral straightener can be well known and reliably replicated if necessary, and images taken from arbitrary angles can be algorithmically rotated so as to cause the straightener position from a first phase to align with the straightener position from a second phase, a common axis for first and second images is thereby produced. This common axis greatly facilitates mapping between first and second three-dimensional models and/or first-phase images and second-phase images. Such an arrangement also facilitates combining a first-phase image and a second-phase image into a combined image.

A system according to some embodiments comprises one or more of the following features:

1. An electromagnetic tracking module capable of detecting, optionally with 5 or 6 degrees of freedom, sensors in or near the patient. An example is Ascension Technology Corp.'s model "MedSAFE". Other examples are NDI models "Aurora" and "Polaris";
2. a plurality of sensors, optionally including sensors for detecting transmitted electronic fields or signals, some sensors being integrated with imaging devices or firmly attached to imaging devices, or attachable to the human body, and/or to body-penetrating devices such as catheters.
3. An ultrasound scanner (hereafter "scanner" or "US" or "TRUS" (transrectal ultrasound)). In some embodiments the scanner can display ultrasound images of cross-sections of the body organs. In some embodiments the ultrasound machine includes a transrectal ultrasound transducer (hereafter "US probe" or "probe"). In some embodiments the ultrasound probe is capable of scanning imaging in a plurality of planes.
4. In some embodiments the ultrasound probe includes a needle guide formed as a cannula or other directed passage. Examples are the B&K ultrasound scanner model Vikinh 2400 or model Pro Focus 2202, with transducer models 8551 or 8818;
5. a computing workstation comprising a CPU, memory, display, and software or firmware;
6. image transfer means for transferring digitized ultrasound images to the computing workstation, for example the Imaging Source, Germany, frame grabber DFG/SV1 or DFG/USBs;
7. a tool position controller for directing biopsy or treatment devices into the patient's body, the controller being able to measure and report spatial positions of tools with respect to the imaging device, for example a needle guide on a TRUS transducer, such as for example a Civco Inc. needle guide.
8. Biopsy or/and treatment needles, for example Standard biopsy needles Angiotech Medical Device Technologies Inc. biopsy needles, ProMag™ 18-gage biopsy needles, and Gall Medical 17-gage cryo-treatment needles.
9. Software comprising 3D registration facilitation algorithms, body movement compensation algorithms and modeling facilitation algorithms.

In some embodiments use is made of an intra-urethral catheter which comprises a sensor attached at a specific known location within the catheter. In some embodiments the sensor is positioned at a part of the catheter which will come to be inside a prostate when the catheter is inserted in the urethra at a known depth. In some embodiments the sensor is embedded the catheter has a Foley balloon at a distal end, for inflation within a bladder, thereby helping fix the distal position of the inserted catheter by preventing withdrawal of the distal end of the catheter from the bladder. In some embodiments, optionally including embodiments with such a Foley balloon, the catheter is provided with a "back stopper", which may be a fixed or positionally adjustable stopper which, once in place, prevents an inserted catheter from further advancing along the urethra, such that when catheter is inserted, Foley balloon is inflated and back stopper is in place, the inserted catheter is prevented from moving distally or proximally within the urethra, and a sensor having a known position with respect to the balloon or other portion of the catheter can be immobilized within the body, providing a fiduciary landmark as mentioned above. Optionally, the sensor can be removed and reinserted into the catheter at a standard position within the catheter. In some embodiments a sensor reporting measurements while being moved within a catheter is used to detect the detail of the urethra location as disclosed by the catheter position. In some embodiments the catheter is a single use device and the sensor is a multi-use device. In some embodiments, the catheter has a rigid or semi-rigid section which is optionally positioned so as to be within the prostate when the catheter is inserted in the urethra and immobilized there, the rigid or semi-rigid section thereby providing increased positional and orientational stability to the prostate;

According to an aspect of some embodiments of the present invention there is provided a system for locating lesions in a prostate during a first intervention session, and for using that lesion location information during a second intervention session, the system comprising A) A first 3D modeling module which creates a first 3D model of the prostate based at least in part on real-time ultrasound imaging of the prostate during a first intervention session;

B) An intervention recording module which records positions of a plurality of biopsy samples taken during the first intervention session, position of the samples being recorded in terms of the 3D model;

C) A diagnosis recording module for recording positions of at least one lesion detected by pathology examinations of the biopsy samples, the lesion positions being recorded in terms of the first 3D model;

D) A second 3D modeling module which creates a second 3D model of the prostate based at least in part on real-time ultrasound imaging of the prostate during a second intervention session;

E) A lesion position calculation module which calculates positions of the detected lesions with respect to the second 3D model, based on positions recorded by the diagnostic recording module and further based on positional relationships between the first 3D model and the second 3D model; and F) A display module which displays the calculated lesion positions in a context of the patient's prostate's real-time position, thereby enabling a surgeon to guide therapeutic interventions during the second intervention session according to lesion location information gleaned during the first intervention session and during analysis of biopsies taken during the first intervention session, the system characterized in that it further comprises at least one of:

G) a module for detecting and reporting the position of a prostate in real time, which module comprises one or more electronic signal transmitters positionable near a patient and a sensor for detecting and reporting the sensor's position with respect to electronic signals transmitted by the transmitters, the sensor being provided on a Foley catheter which comprises a distal balloon inflatable within a bladder for immobilizing a distal end of the catheter and a 'back-stopper' immobilization device for immobilizing a proximal portion of the catheter at the entrance to the urethra, the immobilization devices serving to immobilize the sensor within a prostate at a known and fixed position between the distal catheter end at the bladder entrance and the urethra entrance at the apex of the prostate;

H) an image registration system for mapping first-session 3D model information to a second-session 3D model, which image registration system comprises (i) a user interface which comprises graphical tools by which a user may mark, on a first image derived from real-time imaging of the prostate during the first intervention and on a second image derived from real-time imaging of the prostate during the second intervention, observed positions of bladder-side and apex-side extremities of the prostatic urethra, thereby defining a prostate axis extending between the marked positions of the prostatic urethra extremities in each image; and (ii) a model-aligning module programmed to align the first and second 3D models by 1) marking the prostate axes on the first and second 3D models;

2) overlaying the first 3D model on the second 3D model in a common virtual space;

3) rotating and resizing the first 3D model so that the prostate axis of the first model is co-located with the prostate axis of the second model;

4) rotating the first model in a stepwise fashion around the prostate axis of the first model to produce a set of rotated views of the first model, and calculating for each such view a measure of difference between the rotated view of the first model and the unrotated second model;

5) selecting that rotated view of the first model for which the calculated measure of differences is smallest; and 6) transferring data positions recorded in the first model, in their rotated positions in the selected rotated view, to corresponding positions in the second model; and I) a prostate modeling facilitation tool which comprises (i) a set of predefined 3D models of the prostate, each of the pre-defined models representing one typical type of prostate shape and each model comprising designated positions for bladder-end and apex-end extremities of the urethral prostate; and (ii) an interface operable to present real-time images of the patient's prostate and also graphical displays of the predefined prostate models, and whereby the user may select, from among the set of predefined models, that model which in his opinion best resembles the shape of the patient's prostate, and wherein the first and second modeling modules utilize the selected predefined 3D model in constructing the first and second 3D models.

According to an aspect of some embodiments of the present invention there is provided a device for detecting and reporting the position of a prostate in real time, which device comprises one or more electronic signal transmitters positionable near a patient and a sensor for detecting and reporting the sensor's position with respect to electronic signals transmitted by the transmitters, the sensor being provided on a Foley catheter which comprises a distal balloon inflatable within a bladder for immobilizing a distal end of the catheter and a 'back-stopper' immobilization device for immobilizing a proximal portion of the catheter at the entrance to the urethra, the immobilization devices serving to immobilize the sensor within a prostate at a known and fixed position between the distal catheter end at the bladder entrance and the urethra entrance at the apex of the prostate.

According to an aspect of some embodiments of the present invention there is provided an image registration system for mapping a first-session 3D model of a prostate derived from first-session imaging of the prostate during a first intervention to a second-session 3D model of the prostate derived from second-session imaging of the prostate during a second intervention, which image registration system comprises (a) a user interface which comprises graphical tools by which a user may mark, on a first image derived from real-time imaging of the prostate during the first intervention and on a second image derived from real-time imaging of the prostate during the second intervention, observed positions of bladder-side and apex-side extremities of the prostatic urethra, thereby defining a prostate axis extending between the marked positions of the prostatic urethra extremities in each image; and (b) a model-aligning module programmed to align the first and second 3D models by
  (i) marking the prostate axes on the first and second 3D models;
  (ii) overlaying the first 3D model on the second 3D model in a common virtual space;
  (iii) rotating and resizing the first 3D model so that the prostate axis of the first model is co-located with the prostate axis of the second model;
  (iv) rotating the first model in a stepwise fashion around the prostate axis of the first model to produce a set of rotated views of the first model, and calculating for each such view a measure of difference between the rotated view of the first model and the un-rotated second model;
  (v) selecting that rotated view of the first model for which the calculated measure of differences is smallest; and
  (vi) transferring data positions recorded in the first model, in their rotated positions in the selected rotated view, to corresponding positions in the second model.

According to some embodiments of the invention the system further comprises displaying the second model and the data positions transferred from the first model on a display in a common virtual space.

According to an aspect of some embodiments of the present invention there is provided a prostate modeling facilitation tool which comprises
  (a) a set of predefined 3D models of the prostate, each of the pre-defined models representing one typical type of prostate shape and each model comprising designated positions for bladder-end and apex-end extremities of the prostatic urethra; and
  (b) an interface operable to present real-time images of the patient's prostate and also graphical displays of the pre-defined prostate models, and whereby the user may select, from among the set of predefined models, that model which in his opinion best resembles the shape of the patient's prostate, and
  (c) a 3D modeling system which combines real-time information gleaned from an imaging modality imaging a prostate with information contained in the selected pre-defined model to produce a resultant 3D model which comprises information from both sources.

According to some embodiments of the invention, the tool further comprises a display which displays the resultant 3D model, showing the selected predefined model and the real-time information in a common virtual space.

According to some embodiments, the system further comprises a servomechanism, the system being operable to use the servomechanism to direct a treatment tool to a site calculated by the lesion detection module to be at or near a position of a detected lesion.

According to an aspect of some embodiments of the present invention there is provided a system for characterizing a site of a surgical intervention, comprising
  a) one or more electronic signal transmitters positionable near a patient;
  b) a first sensor attached to a proximal portion of a rectal ultrasound transducer and operable to report detection of signals transmitted by the transmitter;
  c) a second sensor attached to at least one of
    (i) an surgical needle insertable in a patient; and
    (ii) a 'gun' or holder of a surgical needle insertable in a patient; and
  d) a controller operable to receive data from the first and second sensors and to calculate based on the data a position of a distal tip of the surgical needle.

According to some embodiments of the invention the controller is further operable to record the calculated position in context of a 3D coordinate system.

According to some embodiments of the invention, the controller is programmed to record the calculated position when the needle is used to take a biopsy sample.

According to an aspect of some embodiments of the present invention there is provided a system for 3D modeling of a prostate which comprises
  a) a electronic signal transmitter positionable near a patient;
  b) a sensor insertable in a prostate and operable to report changes in reception of signals transmitted by the transmitter;
  c) a controller operable to detect and quantify movement of the prostate based on changes in reception of signals reported by the sensor; and
  d) a 3D modeling system which calculates a 3D model of a prostate based on a set of 2D 'slice' images of the prostate, and which takes into account when calculating the 3D model variations in apparent position of the prostate on individual 'slice' images as a function of prostate movement detected by the sensor during creation of the 2D prostate images.

According to some embodiments of the invention, the sensor is mounted in a catheter insertable into a prostatic urethra.

According to some embodiments of the invention, the catheter comprises a Foley balloon which when inflated prevents withdrawal of a distal end of the catheter from a bladder, and the catheter further comprises a 'back stopper' which limits limits the extent to which the catheter can be inserted into the urethra.

According to an aspect of some embodiments of the present invention there is provided a method of 3D modeling of a prostate which comprises
  a) selecting from among a set of models of typical prostate shapes a model which resembles a shape of a prostate observed in real time;
  b) identifying an axis between two anatomical landmarks observed on the observed prostate;
  c) aligning the selected model with a model of the observed prostate by aligning the anatomical landmarks on the observed prostate with corresponding anatomical landmarks on the selected model; and
  d) rotating, to a plurality of positions, the selected model around an axis between the corresponding landmarks, and for each of the plurality of positions, calculating a similarity value between the rotated model and the model of the observed prostate; and
  e) selecting from among the plurality of rotated positions, the position of the selected model which is calculated to be most similar to the model of the observed prostate.

According to an aspect of some embodiments of the present invention there is provided a system for 3D modeling a prostate which comprises a controller which issues instructions to a user, which instructions direct the user to modify positioning of an ultrasound transducer inserted in a patient in a manner calculated to facilitate aligning a real-time image produced by the transducer with a pre-existing image of a prostate.

According to an aspect of some embodiments of the present invention there is provided a method for transferring diagnostic information about a prostate gleaned from a first prostatic intervention to a 3D model created during a second prostatic intervention, comprising inserting a straightener with known geometry into a prostatic urethra during both the first intervention and the second intervention, thereby constraining the prostate to be similarly arranged during both interventions, thereby facilitating mapping of information from the first information onto the model created during the second intervention.

According to some embodiments of the invention, the method further comprises rotating at least one image from the first intervention around an axis corresponding to an axis of the straightener, thereby causing the rotated image to align with an image from the second intervention.

According to some embodiments of the invention, the method further comprises rotating at least one image from the second intervention around an axis corresponding to an axis of the straightener, thereby causing the rotated image to align with an image from the first intervention.

According to some embodiments of the invention, the method further comprises aligning a first image created during the first intervention with a second image created during the second intervention, the aligning process comprising positioning the first and second images in such a way that position of the straightener in the first image coincides with position of the straightener in the second image.

According to some embodiments of the invention, the method further comprises aligning a first 3D model based on images created during the first intervention with a second 3D model based on images created during the second intervention, the aligning process comprising positioning the first and second models in such a way that position of the straightener in the first model coincides with position of the straightener in the second model.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. [IF IMAGES, REPHRASE] With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 11 is an illustration of a 3D surface model created by contouring, according to an embodiment of the present invention;

FIGS. 16A and 16B are simplified schematic showing a urethral straightener used as an organ-constraining device, according to an embodiment of the present invention;

DESCRIPTION OF SPECIFIC EMBODIMENTS OF THE INVENTION

Figure 1:
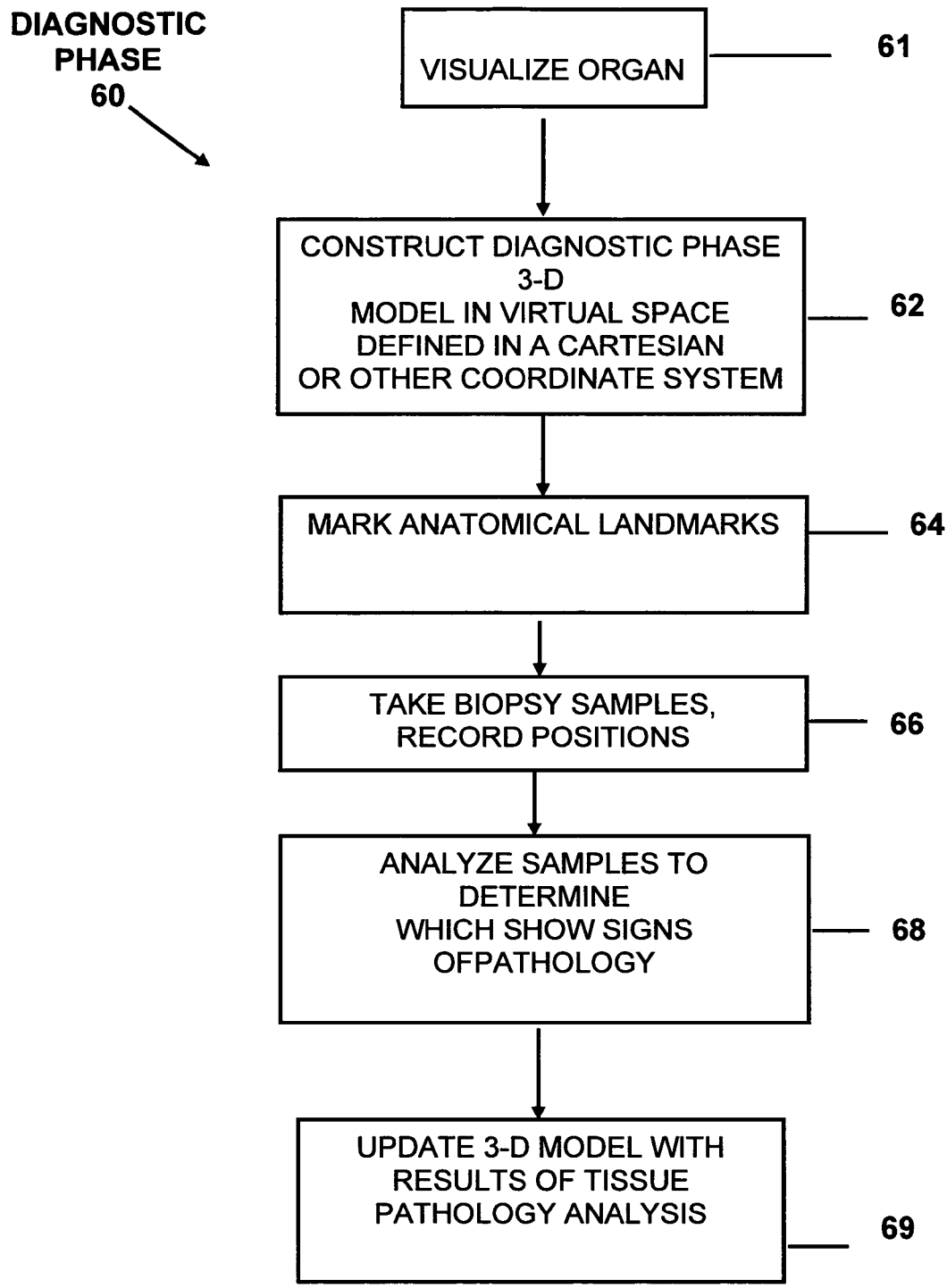
FIG. 1 is a simplified flow chart of diagnostic phase activities of a method for diagnosis and treatment of a patient, according to an embodiment of the present invention.

The present invention, in some embodiments thereof, relates to devices and methods for collecting information during a diagnostic process and using the collected information to guide a subsequent treatment process and/or an additional diagnostic process. Specifically, the present invention can be used to diagnose locations of lesions within a body organ during a first diagnostic phase of medical activity, and use that information to guide therapeutic acts during a subsequent second treatment phase of activity.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In discussion of the various figures described hereinbelow, like numbers refer to like parts. The drawings are generally not to scale. For clarity, non-essential elements are omitted from some of the drawings.

Example of Use of Methods and Devices Described Herein:

A medical procedure according to some embodiments starts with physician's free hand insertion of a trans-rectal ultrasound (TRUS) into the rectum of a patient and his use of the TRUS to create and collect in a computer memory a series of two-dimensional ultrasound segment images, typically in transverse mode. At the time of creation of each of the ultrasound images measurements are taken and recorded showing the spatial location and orientation of the transducer with respect to the patient. In some embodiments this is accomplished by use of a sensor mounted on the ultrasound transducer and reporting (in six degrees of freedom) its orientation and position.

At the same time, in some embodiments measurements are also taken and recorded from one or more sensors (also with six degrees of freedom) which measure body position of the patient. These sensors may be attached externally to the body and/or may be inserted into the patient, for example by being mounted within a catheter and the catheter inserted into the patient's urethra. An electromagnetic transmitter emitting a signal detectable by the sensor(s) enables the sensor to report information defining the sensor's position within a three-dimensional coordinate system related to the position of the electromagnetic transmitter.

Typically the physician scans the prostate from the apex up to the base and the information (images and sensor readings) are taken every 0.1 seconds. Typically about 100 such images may be created, although fewer or more image may be created as desired by an operator. In order to create a 3D model of the prostate a software algorithm running on a system computing device selects a set of images from selected positions (for example 5 mm apart) along the longitudinal axis of the prostate. This set of images is presented consecutively on the screen to the user who, manually or with computer assistance, identifies and marks the border of the prostate, and optionally also the borders of the urethra and/or of other anatomical features. Typically about 10 such images are selected, though a larger or smaller number may be used. It is noted that although such images are generally approximately parallel, images used need not be exactly parallel because, as explained elsewhere herein with respect to some embodiments, exact positioning information relating to each image can be detected and recorded by the system, and taken into account in calculations described herein.

Optionally alternatively, anatomical feature recognition can be done by an image analysis algorithm. In this case, since user intervention is not required for feature recognition, it may be convenient to select a larger number of images for feature recognition from among all images created, or it may be convenient to use all images created. Since each image is associated with information defining where the image source was and how it was oriented at the time the image was taken, objects in the image can thereby be located (i.e. their location can be defined and recorded) in real space as defined by a common coordinate system. In particular, the position of anatomical features marked by the user or identified by an image analysis algorithm can be calculated and recorded as a set of coordinates within a 3D coordinate system.

Background information concerning known techniques for accomplishing some algorithmic manipulations referred to herein are discussed in *Mathematical Models for Rregistration and ApplicationsTto Medical Imaging* By Otmar Scherzer, Editor Springer publishing, ISBN 978-3-540-25029-6, and yet other techniques are well known in the art.

During or upon completion of the process described in the preceding paragraph, a 3D model such as a cross-sectional contour model showing a surface rendering of the prostate and placement of the urethra within the prostate is built by computer algorithms and is presented on to the user on a display in the context of a three-dimensional coordinate system. Additional analyses can be carried out and displayed to the user at this time. For example, the prostate main axis vector can be determined by plotting a vector that joins the center of area of each of the two-dimensional segmented ultrasound images.

Well known display manipulations (pan, zoom, rotate etc.) may be provided. User manipulation of transparency level of the manipulated image may also be provided. This feature enables to user to study space internal to the model during later phases of the procedure, for example to observe a biopsy needle trajectory or to study biopsy locations. In some embodiments a contouring algorithm based on a multipoint curve fitting spline method is used.

In some embodiments a 3D model is created using a method referred to herein as the "Fast 3D" method, and which may be described as follows: The system comprises a set of canonic models. These are 3D surface rendered models of the prostate with typical sizes and shapes. These models are stored in the system memory and can be displayed to the user, who selects the pre-defined model which in his opinion most closely resembles the displayed shape of the patient's prostate as displayed to him as described above. In other words, the user selects "by eye" a one of the canonical shapes available in the system which seems most similar to the modeled 3D shape that was created (as described above) based on actual ultrasound images.

The selected canonical shape is then mapped to the current model by adjusting size and position of the canonical model to at least approximately fit the observed size and position of the current model, the system remembering for future use whatever geometrical changes or distortions were required to achieve a good fit. Geometrical algorithms and optionally linear fitting tools may be used to effect this mapping. (See for example Scherzer op. cit.). To further facilitate this mapping process, each of the canonical models comprises marked positions corresponding to strategic landmarks, for example, entrance and exit points of the urethra to and from the prostate, prostate borders, widest point along the prostate length, etc. After scanning the prostate as described above, the physician selects and marks several of these strategic locations on images of the actual prostate or on images of the prostate 3D model, and the system records the corresponding 3D spatial locations of these marked location in terms of the 3D coordinate system. The algorithmic model matching system then uses the correspondence between specific landmarks marked both on the canonical model and on the observed model to help align the two models, adjusting the detailed canonical model to the observed size and position of the actual prostate. This enables rapid formation and screen presentation 'canonized' 3D model imitating the actual organ and having correct (optionally real-time) dimensions and spatial location and orientation.

In some embodiments, landmark points marked by the user can also be use to estimate the volume of the prostate, Such a set of points can also be used to automatically select one of a plurality of canonical models that best fits the observed prostate, e.g. by calculating distances between points of the set of points, and selecting that model having proportions most similar to the proportions observed on the actual organ.

In some embodiments, with a 3D model of the prostate on the user's screen, the user can manipulate the TRUS transducer in order to observe a predicted trajectory of a biopsy needle or treatment needle on screen in real time.

Upon reaching a selected area of interest for biopsy the user inserts a biopsy needle through a needle cannula. The needle tip location can be seen both on the ultrasound system screen (using a longitudinal view) and on the constructed 3D model. One or more spatial location sensor on the ultrasound enables the system to report the real time location of the TRUS transducer and the real-time position of the inserted needle in a same coordinate system and to display the location of the TRUS and the needle trajectory in real time in the context of the displayed 3D model.

In some embodiments (as shown in detail below) the trajectory of a biopsy needle and position of a distal tip of a biopsy needle or other intervention tool can are calculated and displayed based on information provided by a position sensor (optionally with six degrees of freedom) attached to a proximal portion of a needle or on a needle gun. Given the known and calibrated geometrical relations between the TRUS transducer, the needle cannula, the needle sensor, and the needle tip, positions of the ultrasound, of the needle trajectory, and of the needle distal tip can be displayed in the context of the 3D model in real time.

As shown in detail below, body movements and prostate movements can be compensated for using additional electromagnetic sensors on the body and/or within the prostate catheter. These sensors detect changes in detected electromagnetic fields present in the room, which changes can be interpreted by compensation algorithms as changes in position. Using such sensors and compensation algorithms therefore enables to report and display real-time positions of the needle trajectory and/or needle tip within the 3D model irrespective of patient movements.

In some embodiments, local deformations of the prostate caused by pressing the ultrasound transducer toward the prostate can also be detected and compensated for. Since both scanner and prostate positions are known, if the scanner head is too close to the prostate this will be visible on the display of the 3D model, and the system can be set either to alert the user or to estimate and display the resultant prostate deformation using simple geometric algorisms. In some embodiments additional feedback is available from an electromagnetic sensor within the prostate, which detects prostate movements resulting from pressure from the scanner head on the prostate gland.

The method and apparatus described above allow the user to deliver a needle to any desired location within or around a prostate, to treat tissue at, or take a biopsy sample from, that known position, to record location and nature of the operation in the context of the 3D model, and to save that information for future use.

Alignment (registration) methods disclosed herein enable a user to align a 3D model (and its associated intervention information) created during a first session with a new 3D model based on ultrasound images (optionally real-time images) created during a second session, making it possible to present historical information (e.g. biopsy locations) in the context of an organ's current orientation and position. As discussed in detail below, in some embodiments alignment algorithms use information comprised in first-session and second-session 3D models to find translations and rotations required to map one model onto the other, thereby translating biopsy locations recorded in terms of a first-session 3D model into the context of the real-time 3D model available during a second session. In other words, in one possible use the system makes the locations of biopsy samples taken during a first session visible to a surgeon during a subsequent treatment session. Since each biopsy sample is individually identified at that time it is taken, a physician is enabled to treat locations from which samples taken were shown by pathological analysis to be problematic, and has the option of not treating locations from which samples taken were shown to be healthy.

It is noted that procedures for locating first intervention sites and for translating those locations to a real-time second intervention 3D model necessarily comprise some degree of possible error or uncertainty. In some embodiments of the invention, calculations may be made regarding the degree of uncertainty which pertains to various measurements and calculations, and that information is communicated to a user. For example, some methods described herein comprise matching one image to another and/or one 3D model to another. The 'fit' of one image or model to another image or model is generally not perfect, and some degree of approximation or distortion is expected. In some embodiments of the invention this uncertainty is calculated, and the calculated uncertainty may be communicated to a user graphically or by other means. For example, when location information from a first intervention is graphically presented to a user in the context of a model created during a second information, rather than presenting a location as an exact spot, in some embodiments the system can optionally present the location as an area whose size is a measure of the calculated uncertainty of the information, or as a 'cloud' image wherein the density of the 'cloud' at any point expresses a measure of the probability that the first-session recorded location is at the indicated second-session position.

Attention is now drawn to FIG. 1, which is a simplified flow chart of a procedure 60 for diagnosing an organ such as a prostate, according to an embodiment of the present invention.

At 61 the organ is visualized by one or more clinical imaging modalities, used to create a set of one or more diagnostic-phase images, referred to herein as "first images". At 62, an optional diagnostic-phase three-dimensional model of the organ is created. At 64, one or more anatomical landmark sites are identified. Anatomical landmarks may be identified by a user on a 2D image provided by an imaging modality or on a display of the 3D model created at 62, or by algorithmic image analysis of imaging modality images. Procedure 64 may be combined with procedure 61.

At 66 a plurality of biopsy samples are taken (e.g. by insertion of biopsy sampling needles into the organ at various positions), and the position from which each sample is taken is be noted with respect to one or more landmarks. Alternatively, positions from which samples are taken may be noted and recorded in terms of coordinates defined by the 3D model created at 62.

At 68, biopsy samples taken at 66 are analyzed to determine which samples, if any, present signs of pathology such as, for example, malignant cells.

At optional 69, the three-dimensional model created at 62 is updated with results of the pathology exam: since each tissue sample is located with a known location within the model's coordinate system, locations of pathological samples are noted in the model and can be displayed in the context of a display of the model.

Figure 2:
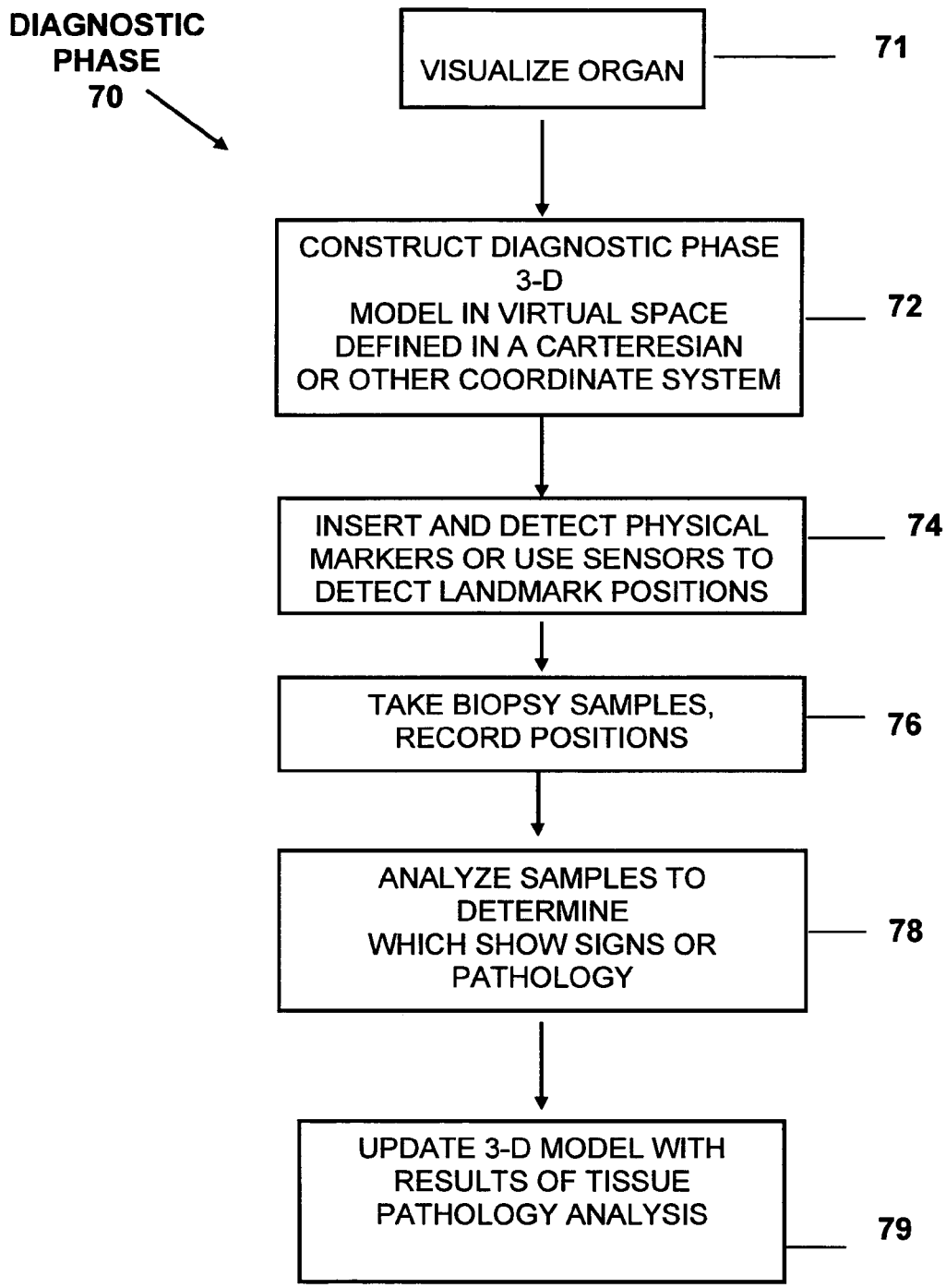
FIG. 2 is a simplified flow chart of diagnostic phase activities of a method for diagnosis and treatment of a patient, according to an embodiment of the present invention.

Attention is now drawn to FIG. 2, which is a simplified flow chart of a procedure 70 for diagnosing an organ such as a prostate, according to an embodiment of the present invention. The flow chart of FIG. 2 differs from the flow chart of FIG. 1 only in that at 74 (corresponding to 64 of FIG. 1) use of physical markers as landmarks is contemplated. These may be of two sorts. One sort are physical markers inserted in a body of a patient or positioned on a body of a patient and which are detectable using an imaging modality. For example, a radio-opaque or ultrasound reflective object might be such a marker, for example a reflective or radio-opaque marker installed in a catheter which is inserted into the prostatic urethra. Another sort is a physical sensor positioned in or on a patient and which is capable of detecting and reporting detection of an environmental field. An example is a sensor installed in a catheter insertable into a prostatic urethra, and capable of detecting and reporting strength of electronic or magnetic fields or signals provided by a field or signal generator provided for the purpose and positioned at a known position with respect to the patient, so that detected strength or identity of one or more fields or signals can be used to calculate the position of the sensor with respect to the patient and/or with respect to the 3D coordinate system of the 3D model. Use of anatomical landmarks as shown at 64 and use of physical landmarks as shown at 74 may be used alternatively or together to provide landmark information for use in locating intervention sites and in aligning images, as discussed elsewhere herein.

Figure 3:
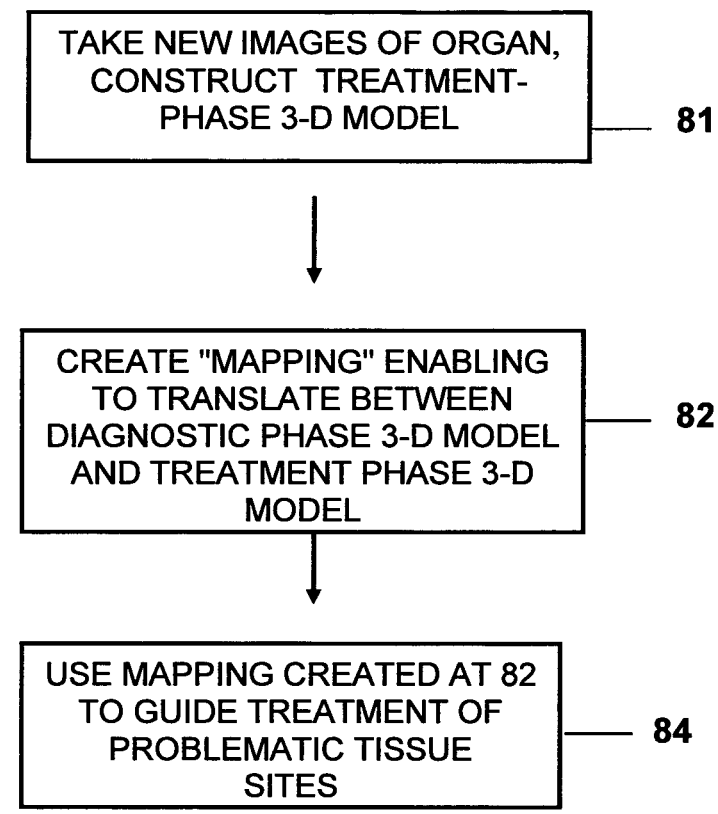
FIG. 3 is a simplified flow chart of treatment phase activities of a method for diagnosis and treatment of a patient, according to an embodiment of the present invention.

Attention is now drawn to FIG. 3, which is a simplified flow-chart of a procedure 80 for treating an organ, according to an embodiment of the present invention.

At 81, the organ diagnosed at 70 is visualized by one or more clinical imaging modalities used to create a set of one or more treatment-phase images, referred to herein as "second images", and an optional second (treatment-phase) three-dimensional model is created.

At 82, a relationship between first and second images and/or first and second 3D models is determined. Procedure 82 may be undertaken automatically, by algorithmic analysis of data, or by interactive process whereby a surgeon or technician inputs elements of image interpretation (e.g. identifying physiological landmarks in an image) to facilitate the process of detecting and determining that relationship. Alternatively and/or additionally, a user may graphically manipulate one or more images to align or match up elements between one or more first images and one or more second images, e.g. by rotating, stretching, squeezing, etc. Landmarks identified at 62 or physical markers were introduced at 72 may be used to align images and/or to determine a mapping (i.e. a method for converting one to another) for relating positions defined in terms the diagnostic-phase 3D model's coordinate system to the treatment-phase 3D model's coordinate system. (As an alternative, a transform mapping second images to first images or to a first three-dimensional model may be determined without actually creating an independent second three-dimensional model.)

It is noted that a diagnostic-phase 3-D model, created at 62 and/or at 72 and marked at 69 and/or 79 contains location information for sites known to require treatment. It is also noted that a treatment-phase 3-D model including diagnostic-phase information created at 69/79 and mapped to a treatment-phase model at 82 contains real-time locations for diagnosed regions of the organ to be treated, which diagnostic information is hence available at the time and place of treatment (e.g. on an operating table).

At 84, sites requiring treatment, and whose real-time positions within the target organ are now known, are treated. Treatment may consist additional diagnostic steps, of ablative therapy by insertion and operation of ablative probes such as cryoprobes, RF probes, or others, or by focusing of intense radiation towards an identified locus (for example using HIFU), or other treatment methods may be used.

Real-time positional information for sites requiring treatment, made available at 82, may optionally be used in various ways. Servomechanisms may be used to direct probes or energy discharges at a treatment site under algorithmic control or under algorithmically assisted direction of a surgeon.

Alternatively, location information may be displayed for a surgeon, who then manually directs treatment towards a site. In particular, a composite image may be displayed on a display, which image combines real-time organ position information and diagnostic-phase information pertaining to sites requiring treatment, both sorts of information displayed on a common image in a common coordinate system, which image also shows to a surgeon real-time feedback regarding positions of therapeutic probes as these are inserted into the organ, thus providing the surgeon with real-time targeting information which includes estimated real-time positions of loci analyzed during diagnostic phase activity, which diagnostic activity may have been obtained at a distant site hours or days previously.

Figure 4:
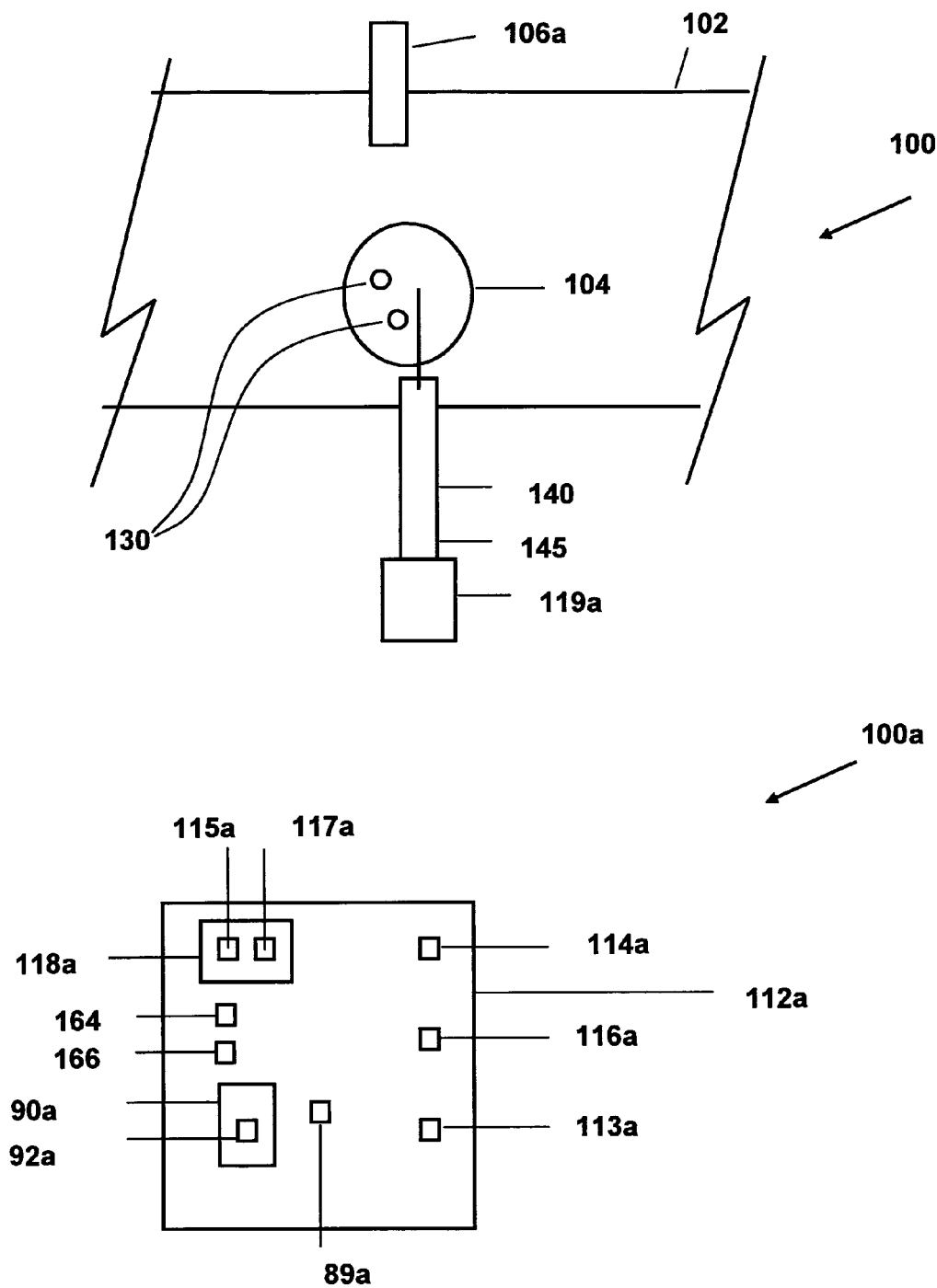
FIG. 4 is a simplified schematic of a diagnostic portion of a system for diagnosis and treatment, according to an embodiment of the present invention.
Figure 5:
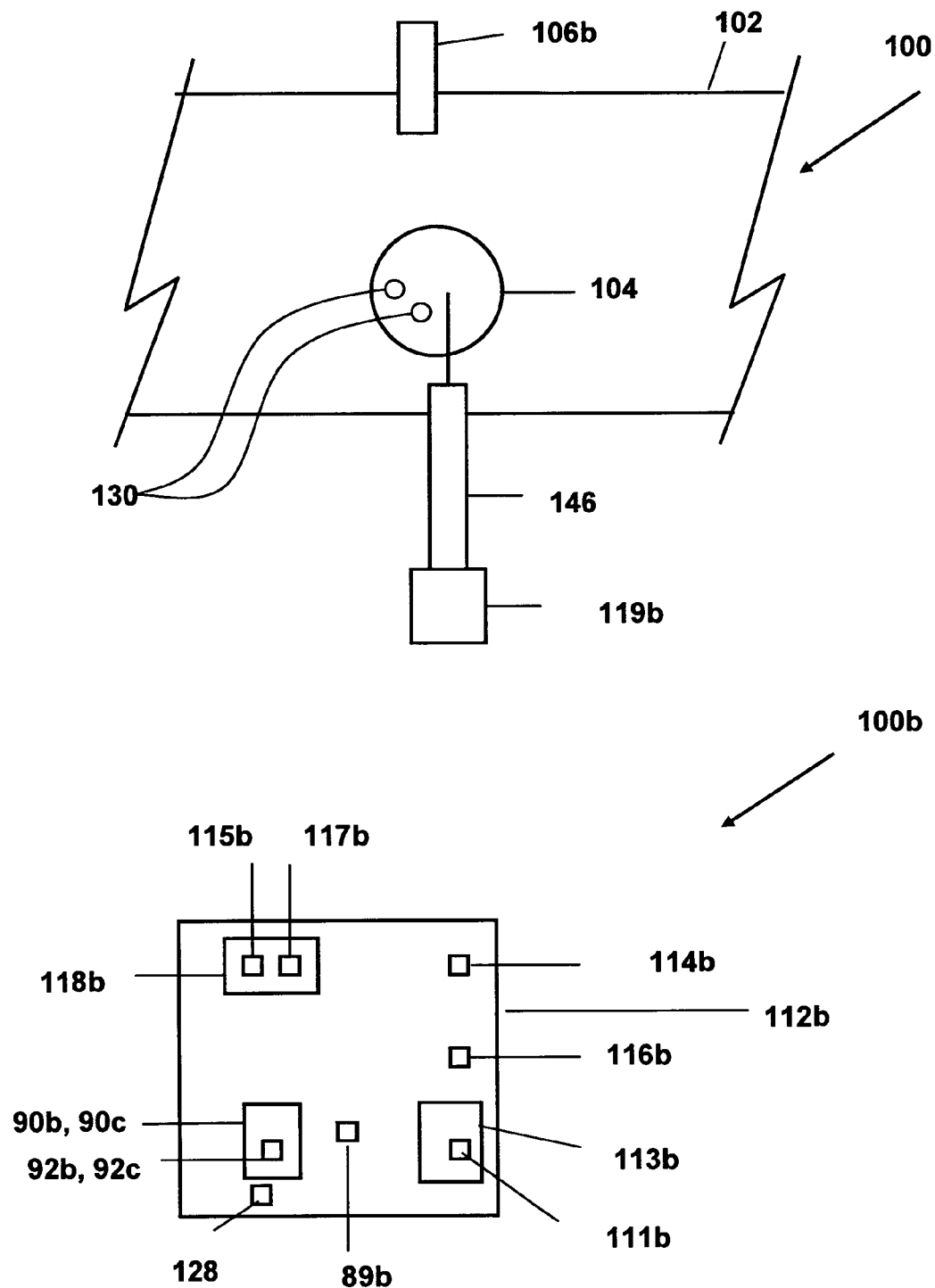
FIG. 5 is a simplified schematic of a treatment portion of a system for diagnosis and treatment, according to an embodiment of the present invention.

Attention is now drawn to FIGS. 4 and 5, which together are a simplified schematic of a system for diagnosis and treatment of a patient, according to an embodiment of the present invention.

FIG. 4 presents a diagnostic portion 100a of a system 100 for diagnosing and treating an organ of a patient, in accordance with an exemplary embodiment.

In FIG. 4, organ 104 of patient 102 is shown, with optional fiducial markers 130 inserted therein. An imaging modality 106a may be an ultrasound probe, an x-ray device, an MRI system, or any other imaging modality or combination of imaging modalities. Information gleaned from operation of imaging modality 106a may be formed as a set of one or more images referred to herein as "first images" 89a. Information from imaging modality 106a is communicated by wired or wireless transmission to a control module 112a, which optionally comprises a display 114a, a memory 116a, a communications interface 166 and an optional mechanical controller 118a, which may optionally comprise a servomechanism control 115a operable to control a servomechanism 119a operable to displace a diagnostic tool 145, and optionally a position sensor 117a for sensing position of diagnostic tool 145.

Communications interface 166 is any communications device which enables controller 112a to connect to the outside world, for example a Bluetooth unit, a USB port, an infrared link, or any other communications device. In some embodiments interface 166 communicates with other hospital systems, for example communicating with systems such as PACS via communication protocols such as DICOM.

In some embodiments, control module 112a is programmed to construct a first three-dimensional model 90a within which information gleaned from imaging modalities 106a is related to a first three-dimensional coordinate system 92a defining a first virtual space. A user interface 113a may be provided, by means of which a user may input information serving to facilitate portions of the diagnostic process. In particular, interface 113a may be programmed to enable a user to identify anatomical landmarks within the first images, which landmarks will also be visible within second images created during a second set of procedures and can be used to facilitate mapping between first and second images and/or between first and second three-dimensional models.

Display 114a is optionally operable to display first images 89a and/or to display images based on three-dimensional model 90a. These images may be used to guide placement of fiducial markers 130 in organ 104, and may be used to guide extraction of tissue samples from a site or plurality of sites within organ 104 by means of a diagnostic tool 145, which may be a biopsy needle 140 or a plurality of biopsy needles 140, or any other diagnostic tool, and which may optionally be guided by servomechanism 119a and/or which may be connected to tool-position sensor 117a. Diagnostic tool 145 is optionally constructed to be visible under imaging modality 106a.

According to methods presented herein, during a diagnostic phase of treatment, locations of sites of biopsy samples taken by diagnostic tool 145, optionally reported by sensor 117a and recorded in memory 116a of control module 112a, may be identified and recorded in terms of coordinate system 92a of 3-D model 90a.

FIG. 5 presents a treatment portion 100b of a system 100 for diagnosing and treating an organ of a patient, in accordance with an exemplary embodiment of the invention.

In FIG. 5, organ 104 of patient 102 is shown with optional fiducial markers 130 inserted therein. An imaging modality 106b may be an ultrasound probe, an x-ray device, an MRI system, or any other imaging modality or combination of imaging modalities. Information gleaned from operation of imaging modality 106b may be formed as a set of one or more images referred to herein as "second images" 89b. Information from imaging modality 106b is communicated by wired or wireless transmission to a control module 112b, which optionally comprises a display 114b, a memory 116b, and a mechanical controller 118b, which may comprise a position sensor 117b for sensing position of a therapeutic tool 146. In some embodiments control module 112b includes a servomechanism control 115b for operating a servomechanism 199b to move a therapeutic tool 146 into and within patient 102. Therapeutic tool 146 optionally comprises materials visible under imaging modality 106b.

In some embodiments control module 112b is programmed to construct a second three-dimensional model 90b within which information gleaned from imaging modalities 106b is related to a second three-dimensional coordinate system 92b defining a second virtual space.

Display 114b is optionally operable to display second images 89b and/or to display images based on three-dimensional model 90b. These images may be used to display organ 104 as it exists during a treatment phase of activity. In addition, as discussed herein, during a treatment phase of activity, locations of sites of biopsy samples taken by diagnostic tool 145, optionally reported by sensor 117a and recorded in memory 116a of control module 112a, and identified and recorded in terms of coordinate system 92a of 3-D model 90a, may be mapped into model 90b and displayed on display 114b in form of a combined (composite) image 128, also referred to herein as common image 128, which combines information from model 90a with information from model 90b, and/or which combines information from first images 89a with information from second images 89b.

A user interface 113b may be provided, by means of which a user may input information serving to facilitate portions of the therapeutic process. In particular, interface 113b may be provide graphical tools enabling a user (e.g. using a mouse or a touch screen) to identify anatomical landmarks within second images 89b, which landmarks can be used to facilitate mapping between first images 89a and second images 89b and/or between first three-dimensional model 90a and second three-dimensional model 90b. In addition to facilities for identifying anatomical landmarks and/or fiducial markers within second images 89b, interface 113b may comprise graphical tools 111b for graphically modifying first and/or second images (e.g. by stretching, by rotation, etc.) to bring about a graphical matching of first and second images, wherein graphical image changes required to bring a first and a second image into alignment one with another provide information usable by control module 112b for mapping first and second 3-D models to each other. Alternatively, graphical manipulations required to align a first-image/second-image pair to each other can be repeated by control module 112b to enable continuous presentation of real-time second images with, superimposed thereon, surgical target location information gleaned from first images.

For simplicity, diagnostic portion 100a and treatment portion 100b are presented separately in FIGS. 4 and 5 respectively. In practice, all or part of portions 100a and 100b may optionally be combined into a common system, wherein, for example, a single element of imaging modality equipment 106 may be used during both diagnostic and treatment phases of activity, and some or all elements of control modules 112a and 112b and servomechanisms 119a and 119b may be implemented by a same set tools for processing, sensing, controlling, displaying, and other functions herein described.

For simplicity of exposition, references in the following disclosure to controller 112 should be understood to refer to controller 112a and/or controller 112b, and similarly with respect to the various component elements of controller 112.

In some embodiments, control module 112b is programmed to combine one or more first images 89a and second images 89b (one or both being optionally graphically modified) into a common image 128. A common image 128 might show, for example, a real-time image of an organ 104 (e.g. a prostate) of a patient 102 ready for treatment, with superimposed thereon a diagnostic-phase image, of the same patient 102 and organ 104, created during diagnostic phase activity at a time when a specific biopsy sample, later found to contain malignant cells, was extracted from organ 104. If a surgeon uses biopsy needles and treatment probes which are visible under his imaging modality, combined common image 128 can provide to the surgeon, without need of three-dimensional modeling, a direct visual indication of the relationship between the position of a surgical treatment target and the real-time changing position of a treatment probe he is inserting in a patient with the goal of ablating that imaged surgical target. Graphical enhancements such as using different colors to distinguish first-image information from second-image information can enhance clarity of common image 128.

Alternatively or additionally, control module 112b can be programmed to construct common image 128 from information provided by first three-dimensional model 90a and from information provided by second three-dimensional model 90b. Further alternatively, control module 112b can be programmed to construct common image 128 from information provided by first three-dimensional model 90a and from information derived from one or more second images 89b.

Common image 128 may be presented as a still image, a series of still images, or as a continuously generated video image. Common image 128, displayed to a surgeon or other user, provides real-time guidance for a surgeon, by creating an image which directly shows whether a currently inserted ablation probe or other treatment tool 146 is correctly positioned with respect to a previously diagnosed treatment target site.

Information gleaned from first and second 3-D models 90a and 90b can also be used to enable automatic or semi-automatic positioning of one or more treatment tools within organ 104, under control of servomechanism control 115b and/or position sensor 117b, and tool placement device 119b, which may be a servomechanism or a manual or semi-automated stereotactic device.

Figure 6:
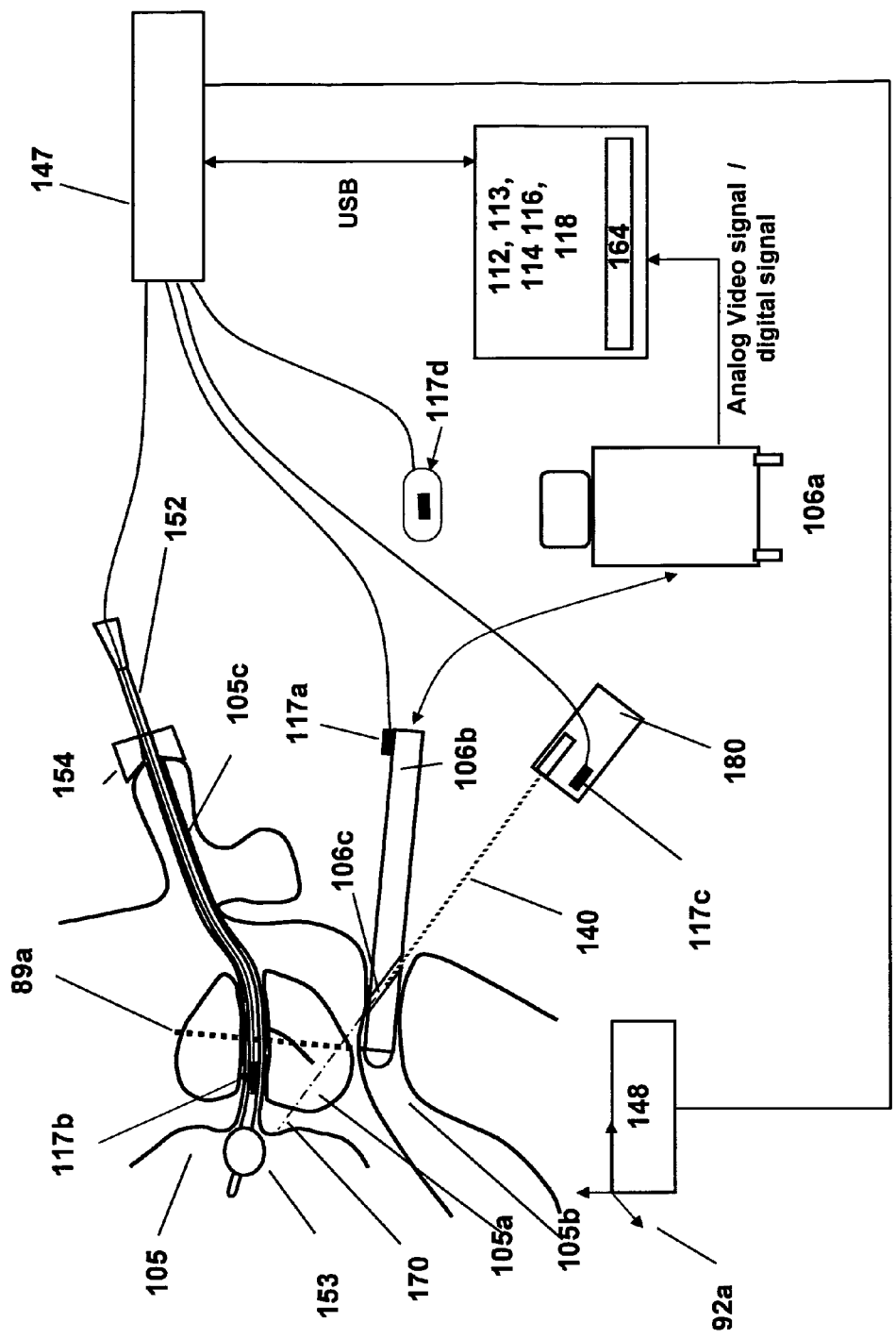
FIG. 6 is a simplified schematic presentation of a system for focused prostate cancer diagnostics and treatment, comprising an ultrasound device with attached electromagnetic sensor, a biopsy needle insertion of which can be guided by ultrasound, and a prostate movement detection sensor located inside a catheter inside a urethra, according to an embodiment of the present invention.

Attention is now drawn to FIG. 6, which presents a simplified schematic of components of a system according to an embodiment of the present invention. The male genitourinary anatomy is sketched on the upper left of the figure, showing the prostate 105a, bladder 105, urethra 105c, and rectum 105b. An ultrasound scanner 106a is in use with transrectal ultrasound (TRUS) transducer 106b placed in the rectum. In some embodiments ultrasound transducer 106b is equipped with a cannula or needle guide 106c for the insertion of biopsy or treatment needles. (Civco needle guides are an example of such guides.)

A transurethral catheter 152 is stabilized in place inside urethra 105c by Foley balloon 153 which prevents withdrawal of catheter 152 out of bladder 105, and by back stopper 154 which prevents catheter 152 from being drawn further into the body. Catheter 152 houses one or more electromagnetic sensors 117b. Sensor 117b is firmly attached at a known location inside the catheter tubing. Therefore, once catheter 152 is inserted and fixed in place by balloon 153 and back stopper 154, any movement of prostate 105a is sensed by the sensor 117b. An additional sensor 117a is firmly connected to transducer 106b and detects the spatial location of both the ultrasound imaging plane and the trajectory of any needle inserted through needle guide 106c (since their geometrical relations are known with reference to transducer 106b). Spatial location of urethra 105c is accurately reported during insertion of catheter 152 with has sensor 117b mounted inside it. Additional sensors 117d can be attached to the patient's body to monitor body movement.

An electromagnetic tracking system 147 (hereafter "EM 147") is used to detect in real time the spatial location of the sensors in the working space. EM 147 includes a transmitter 148 that produces local electromagnetic field within the working space. Sensors 117a, 117b and 117c and optional 117d transmit output signals to EM 147 on the basis of which EM 147 can calculate the spatial location and angular orientation of the transmitting sensor. The output of EM 147 is communicated to controller 112 (112a and/or 112b) and at the same time controller 112 receives ultrasound images or other images from an imaging modality 106a, optionally via a frame grabbing card.

Figure 7:
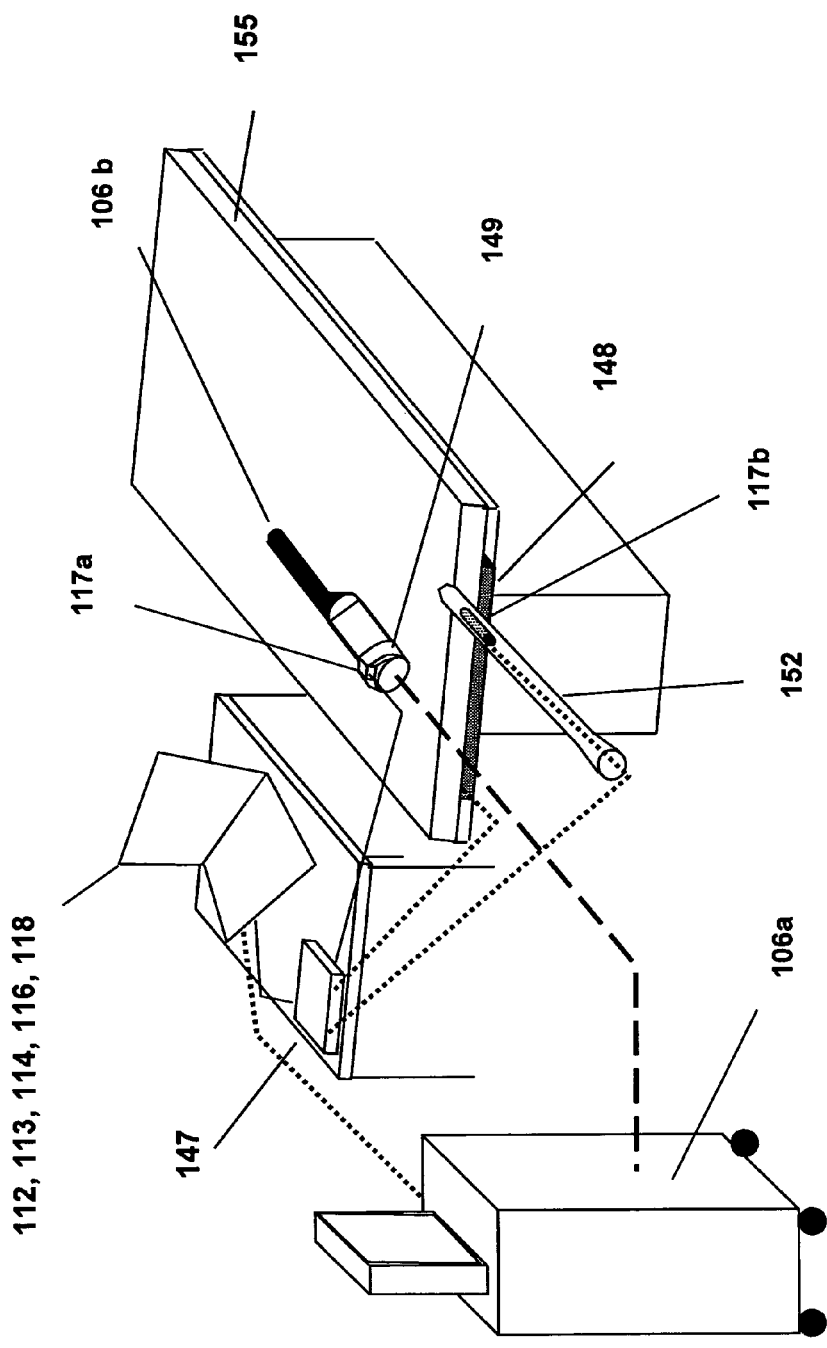
FIG. 7 is a generalized view of a treatment environment, according to an embodiment of the present invention.

FIG. 7 is a simplified schematic presenting an optional and exemplary arrangement of a system near a treatment bed, according to an embodiment of the present invention. A flat electromagnetic transmitter 148 is placed beneath bed mattress 155. A small (e.g. notebook) computer equipped with a frame grabbing card provides the functionality of controller 112 and its components as described herein. A sensor 117a is mounted on an ultrasound transducer 106b. Data flow is shown by dotted lines in the figure: ultrasound signals flow from transducer 106b to ultrasound unit 106a where images are visible on a screen. The video signal is also transferred to controller 112 where a frame grabbing card (not shown) digitizes images for use by controller 112's computational algorithms. Position information is transferred from sensor 117a to EM processing unit 147 and from there to controller 112. Positioning information is also transferred from sensor 117b in catheter 152 to controller 112. The software adds position information received from EM 147 to each of the images received from ultrasound in real time.

Figure 8:
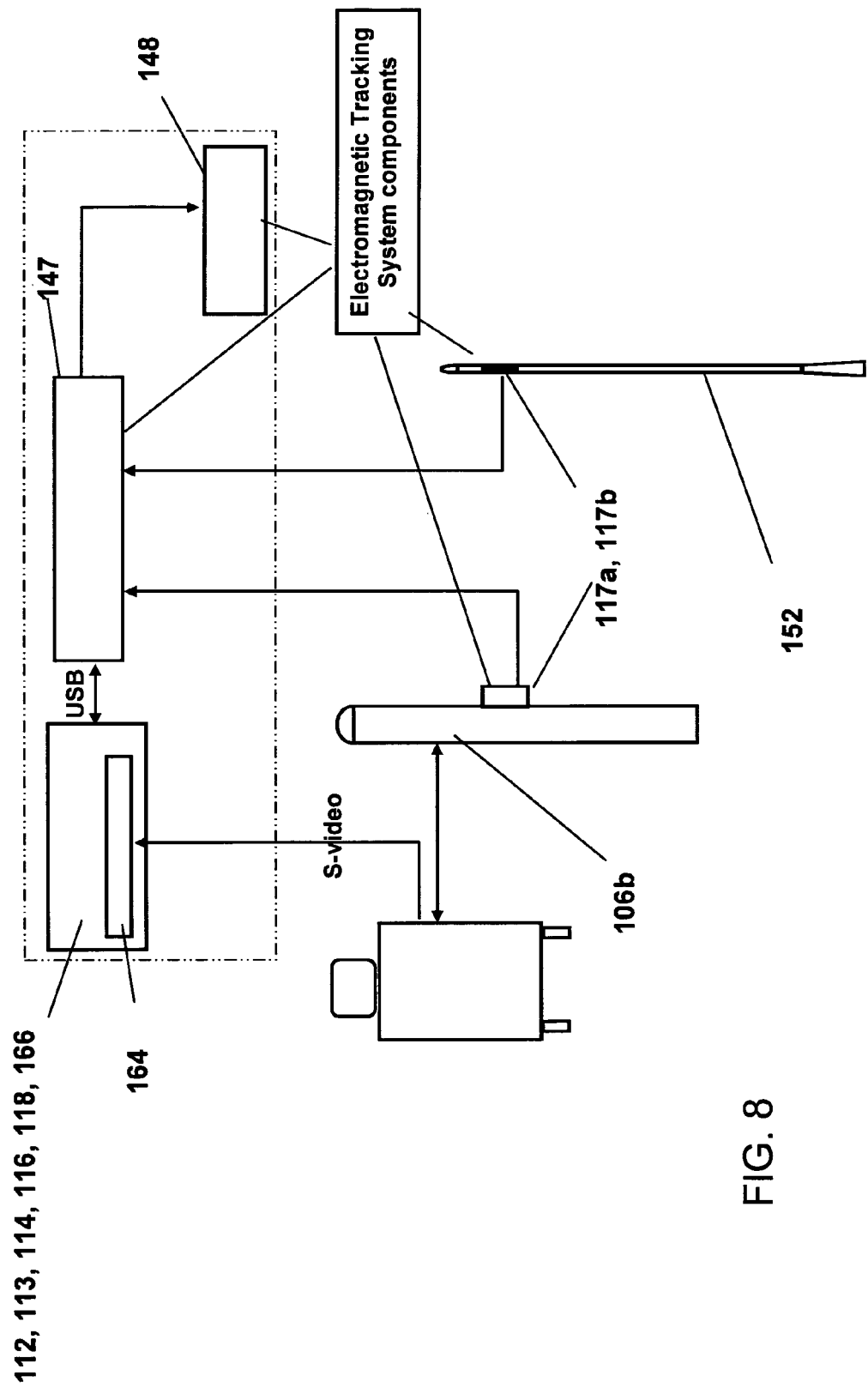
FIG. 8 is an schematic overview of a treatment system showing interfaces between a 3D positioning system, an ultrasound scanner and an ultrasound transducer, enabling collection ad use of 3D spatial information gathered from ultrasound images, according to an embodiment of the present invention.

FIG. 8 presents an addition view of the system shown in FIG. 6, according to an embodiment of the invention. EM system 147 comprises a processing unit also labeled 147, a transmitter 148, and sensors 117b (within catheter 152) and 117a (attached to transducer 106b). Ultrasound system 106 comprises a processing unit 106a, transducer 106b and an optional display. System controller 112 includes a frame grabbing card 164 and processors, software, memory, user interface data storage and data communications interface 116.

Figure 9:
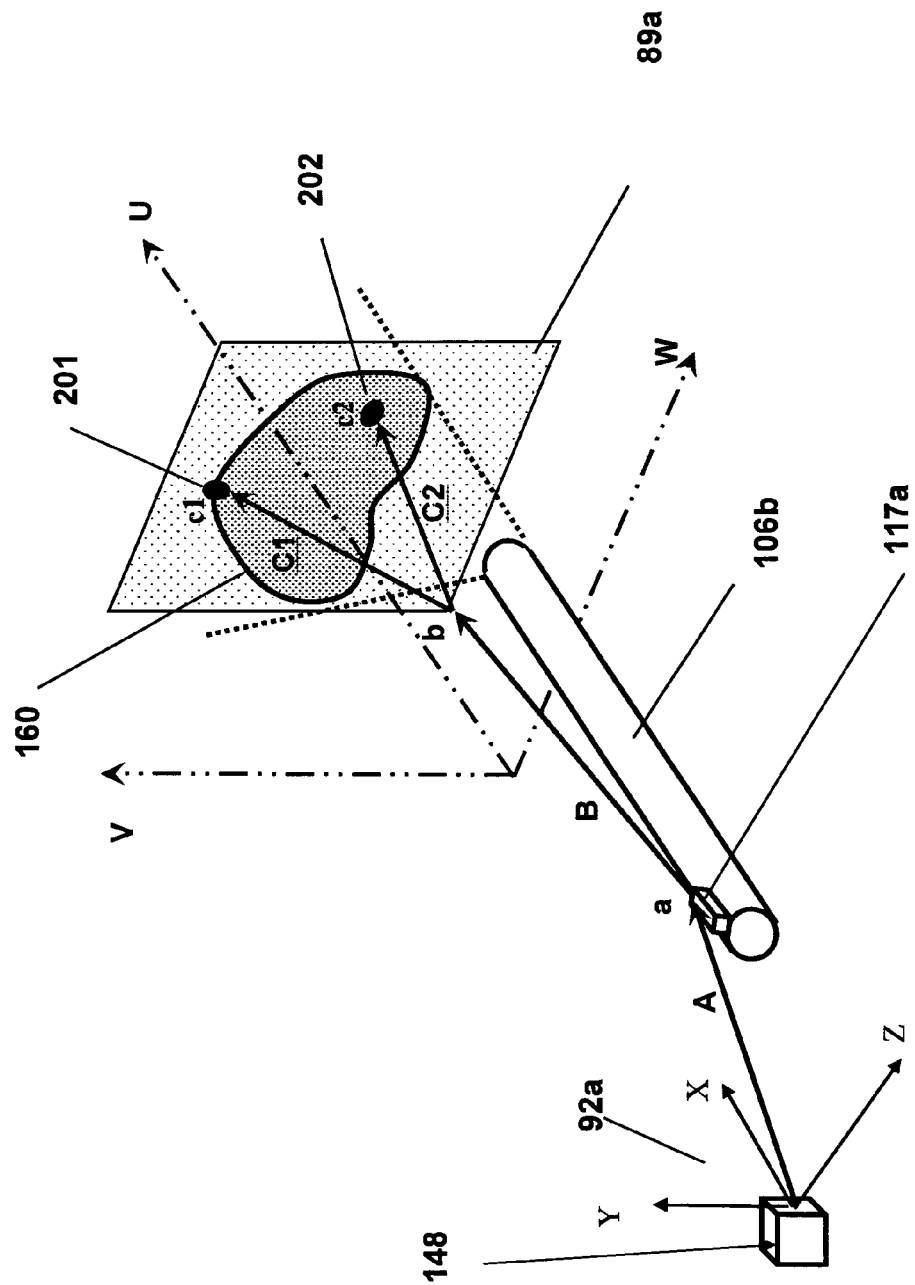
FIG. 9 is a schematic view showing registration of ultrasound image pixels into a 3D coordinate system, according to an embodiment of the present invention.

FIG. 9 is a simplified schematic illustrating registration of ultrasound image pixels in a 3D coordinate system, according to an embodiment of the present invention. The geometric arrangement shown in the figure allows position and orientation calculations and display of user-marked features on ultrasound images. EM transmitter 148 transmits a field detectable by sensor 117a. Vector A and the spatial orientation of point a (position of sensor 117a) are continuously measured by the EM system 147 in terms of a 3D coordinate system XYZ optionally with origin at transmitter 148. Sensor 117a measures six degrees of freedom of its position and orientation. Vector B connects between sensor 117a's location and point b, where b is any selected pixel on an ultrasound image. Point b is identified by its position in a local coordinate system UVW whose origin is at ultrasound transducer 106b. Vector B is measured through calibration or known from the technical data of the transducer (location and orientation of the imaging planes). Vector C1 is a vector in UVW along the ultrasound imaging plane from an identified pixel b up to a point of interest c1. Standard ultrasound tools are used to obtain the calibration data, e.g. millimeters per pixel in both vertical and horizontal directions along the imaging plane. Alternatively calibration can be performed. The position in coordinate system XYZ of each such point of interest such as c1 or c2 is simply a vector summation of A+B+C. When a user uses a computer mouse or touch screen or similar tool to mark a point of interest (e.g. the position of a recognizable anatomical landmark) on the display, controller 112 (not shown in this figure) calculates the location data for the marked feature (based on real-time sensor date reports) and saves the pixel data and the image location data substantially simultaneously. In this manner the spatial position of any point of interest (e.g. c1, c2) is calculated and stored in controller memory.

Contours of the prostate at any selected spatial location can be calculated by interpolation between marked points (e.g. user-marked feature borders) such as c1. (Alternatively, direct 3D interpolation can be used, using the entire data set or using sets of slices.)

Figure 10:
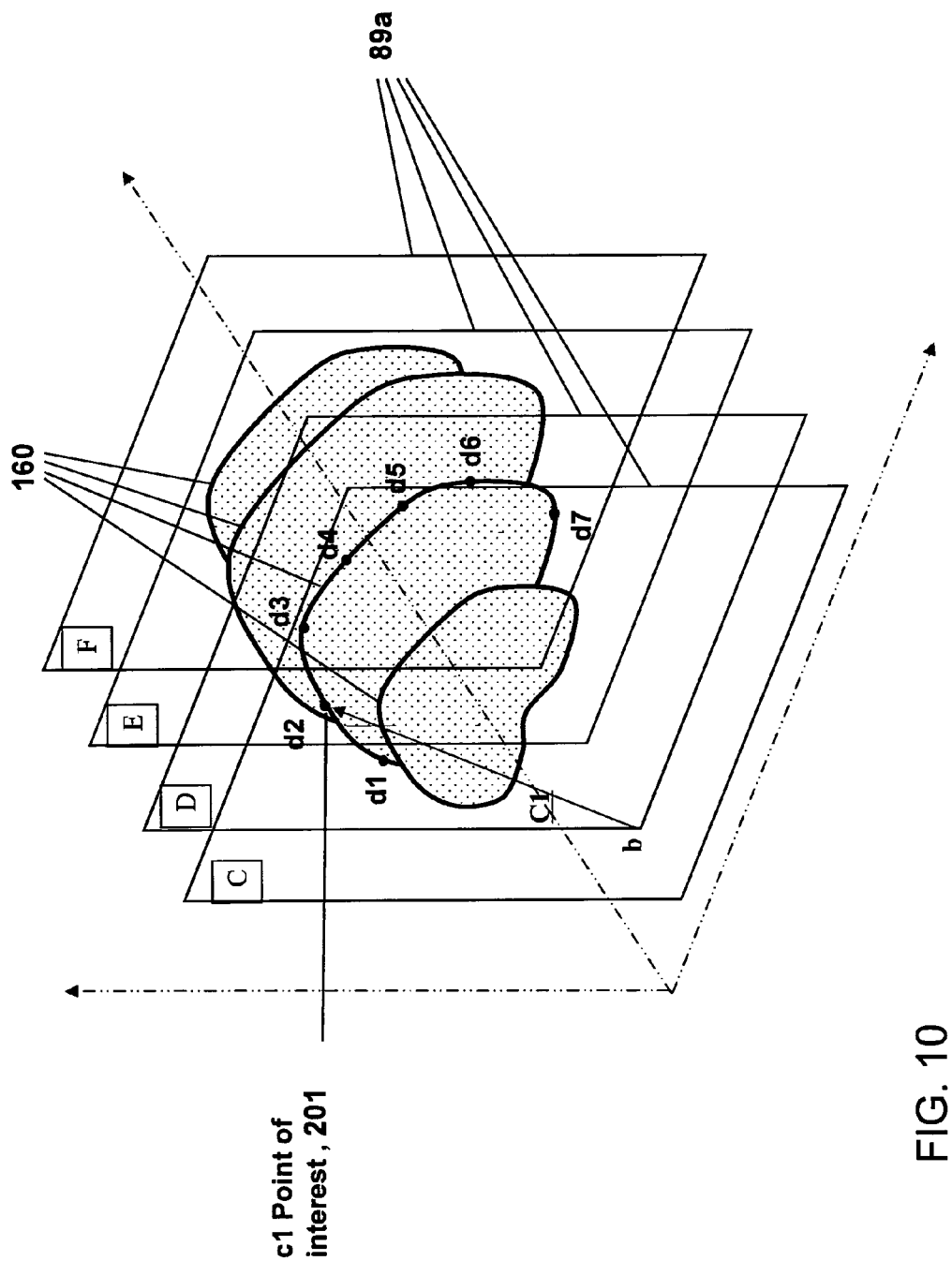
FIG. 10 is a schematic view of a set of 2D slice images useable as a basis for creation of a 3D spatial model of an organ, according to an embodiment of the present invention.

Attention is now drawn to FIG. 10, which illustrates contouring (segmentation) and 3D model creation, according to an embodiment of the present invention. FIG. 10 illustrates the formation of cross-section contour 160 on slice image D of an organ such as a prostate. The user marks border points d1, d2, d3, . . . d7, at least some of the 'slice' images presented by controller 112. Controller 112 then completes the contour using known curve-fitting methods (e.g. interpolation, spline). Marked data points for each cross section (each 'slice') are stored in the computer memory in the XYZ coordinate system. FIG. 10 further illustrates the process of formation and illustration of a 3D model of the organ: cross-section contours on other planes 89a, (e.g. C, E, and F) are made in a manner similar to that described for cross section D. Positions of marked border points in the XYZ coordinate system are known from location of b (see FIG. 9), origin of the image plane for each slice, and from the unique vector (e.g. C1) to each marked or interpolated point.

Once spatial location of the border for all slice planes is determined, a full 3D model of the organ can be created using standard methods and then can be displayed on the controller display. EyeShot viewport control tools from devDept Software, Via Ugo Foscolo, 19, Zola Predosa, BO 40069, Italy, +039(051)7401811 is an example of a system which can create a full 3D model from such data. FIG. 11 shows how, once a 3D model has been created, standard tools can be used for manipulations (rotation, translations, cross section etc.) on a display, to show any desired view.

Figure 12A:
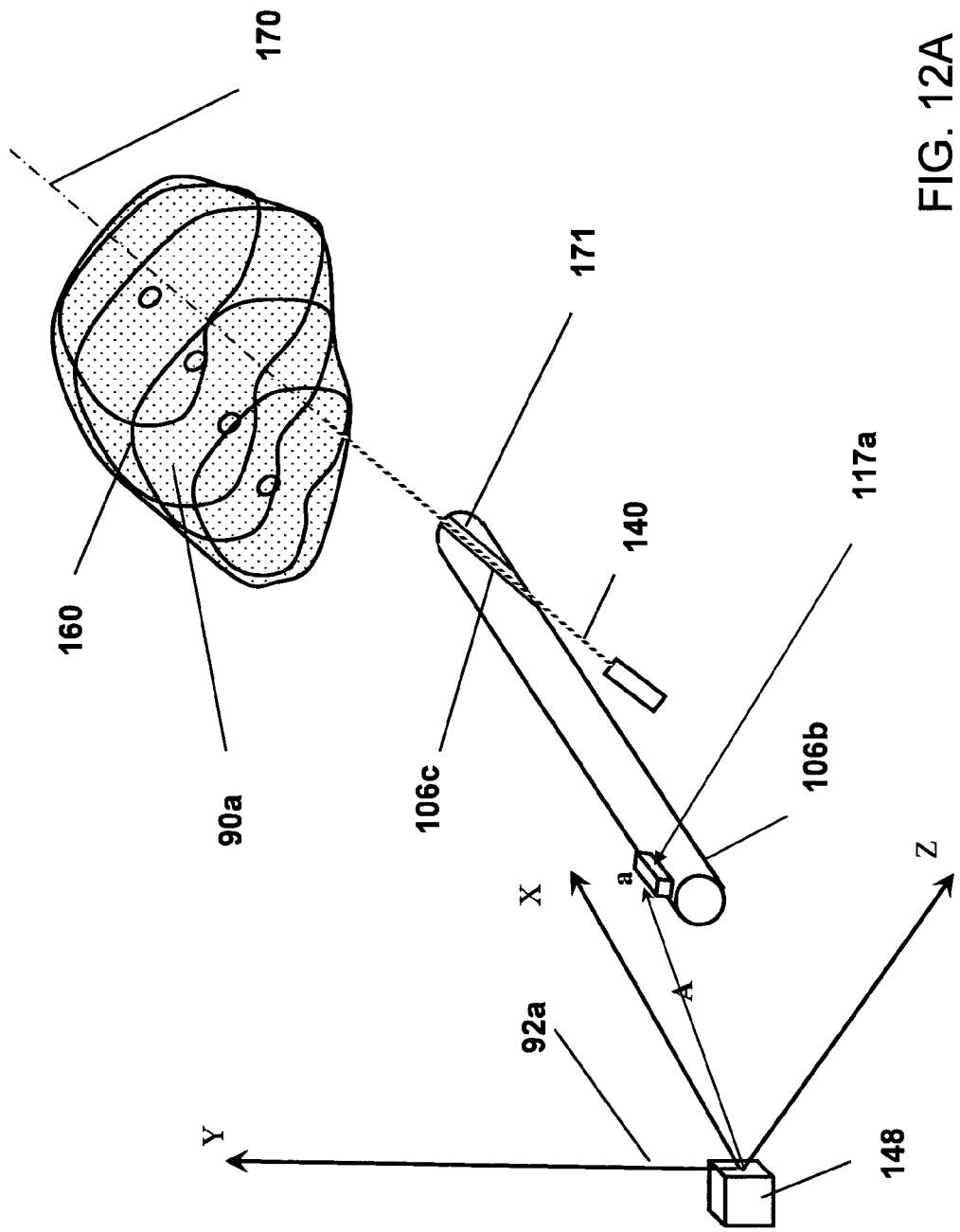
FIGS. 12A and 12B are simplified schematics of a real-time presentation of an expected location of a diagnostic/treatment tool trajectory and tip, respectively, according to an embodiment of the present invention.
Figure 12B:
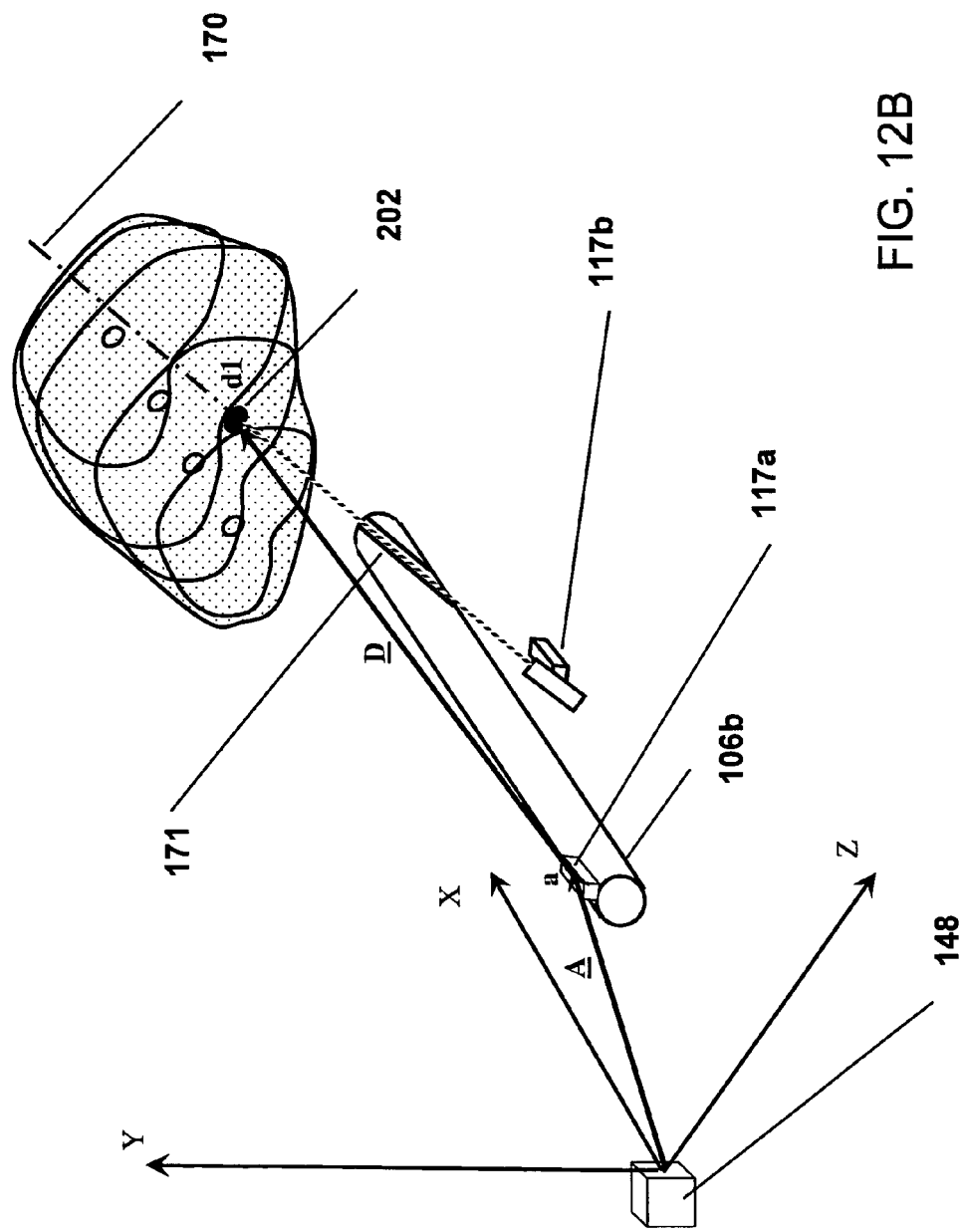

Attention is now drawn to FIGS. 12A and 12B which illustrated real-time presentation of a diagnostic tool or treatment tool in the context of a 3D model, according to embodiments of the present invention.

In FIG. 12A sensor 117a detects position of transducer 106b. The position of needle cannula 106c with respect to transducer 106b is known, or can be determined by one-time calibration to observe the geometrical relation between the position of sensor 117 and the expected trajectory of a needle 171 passing through cannula 106C. Once this calculation is made, the expected real-time trajectory of an inserted needle can be presented on a display in the context of the 3D model.

In FIG. 12B two sensors are used, one (117a) attached to transducer 106b and one (117b) attached to a proximal end an insertable needle 171 (or to a needle gun). Knowing or calibrating the distance between needle sensor 117c and the distal tip of needle 171 allows to calculate and to present on display, in the context of a 3D model of the organ, both the expected needle trajectory and also the real-time position of the needle tip 202.

Figure 13:
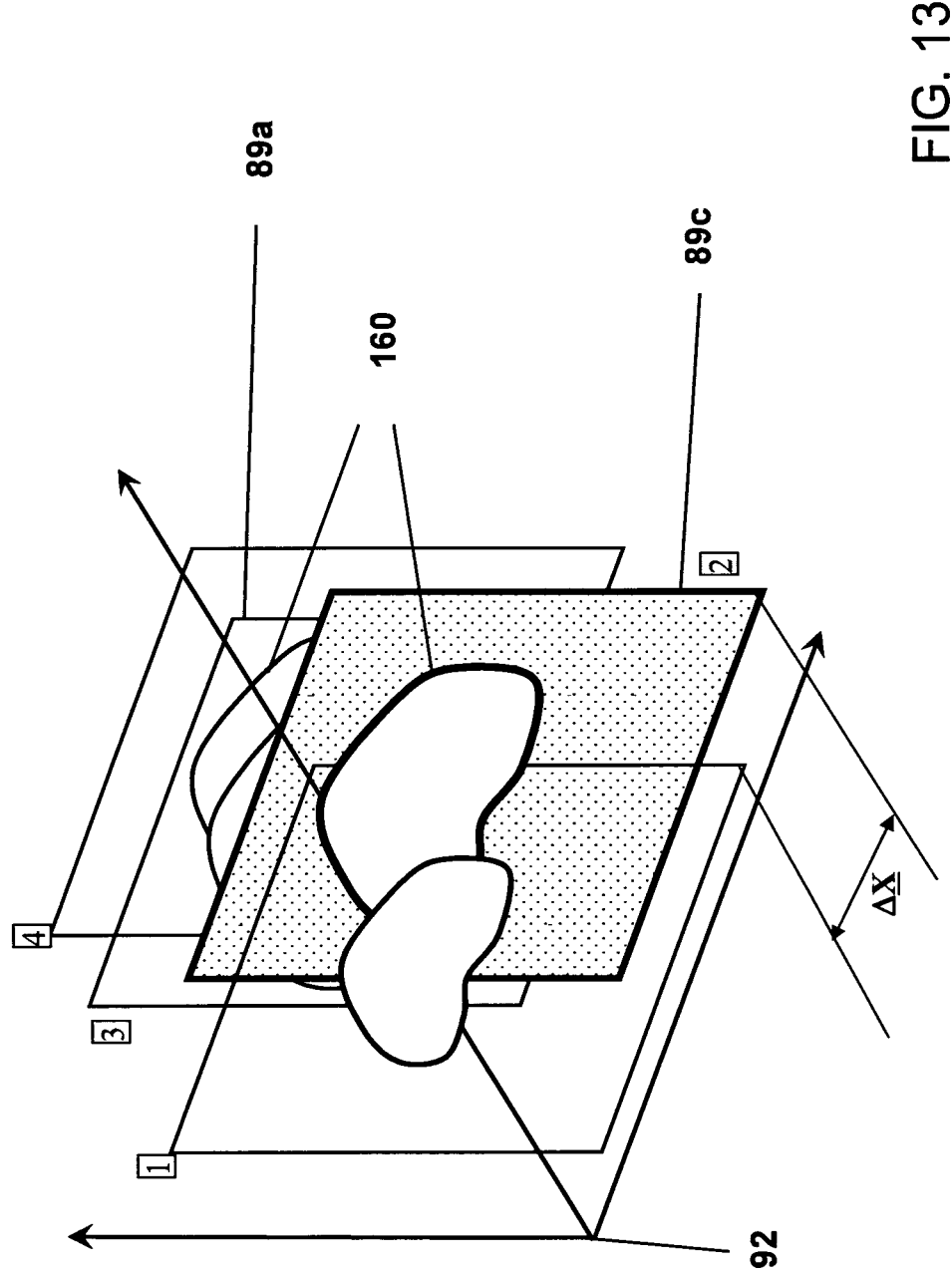
FIG. 13 is a simplified schematic showing movement of an ultrasound image during image acquisition, as quantitatively detected by a sensor inside the urethra, according to an embodiment of the present invention.

Attention is now drawn to FIG. 13, which illustrates handling of a situation where a prostate (or other organ) is displaced during the acquisition of images being used to create a 3D model, according to an embodiment of the present invention. In the simplified exemplary case illustrated here, a momentary displacement of the prostate is reflected in a slice image 89c in which the prostate profile has been displaced sideways. As described above, a sensor within a catheter inserted in the body (e.g. within the prostatic urethra) detects the prostate movement and provides that movement information to controller 112, which uses standard mathematical tools to calculate the required translation of the image to its expected position between the other images, so that the process of creating a continuous 3D model of the prostate can continue as described above.

Attention is now drawn to FIGS. 14A-14D, which illustrates the "Fast 3D" method of creating a 3D model, according to embodiments of the present invention.

Figure 14B:
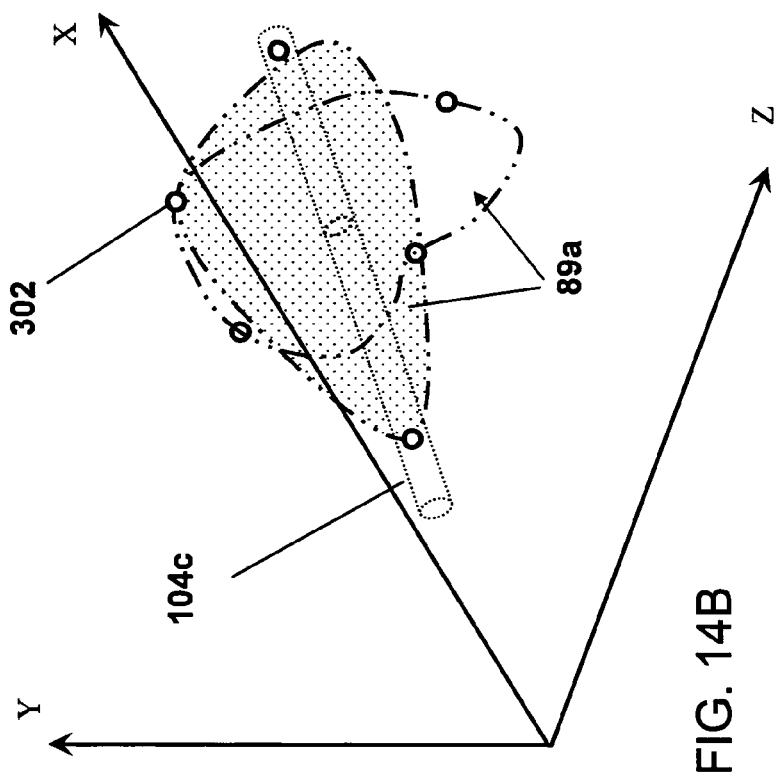
FIG. 14B is a simplified image showing six fitting points marked on an ultrasound image presented on a display, according to an embodiment of the present invention.
Figure 14A:
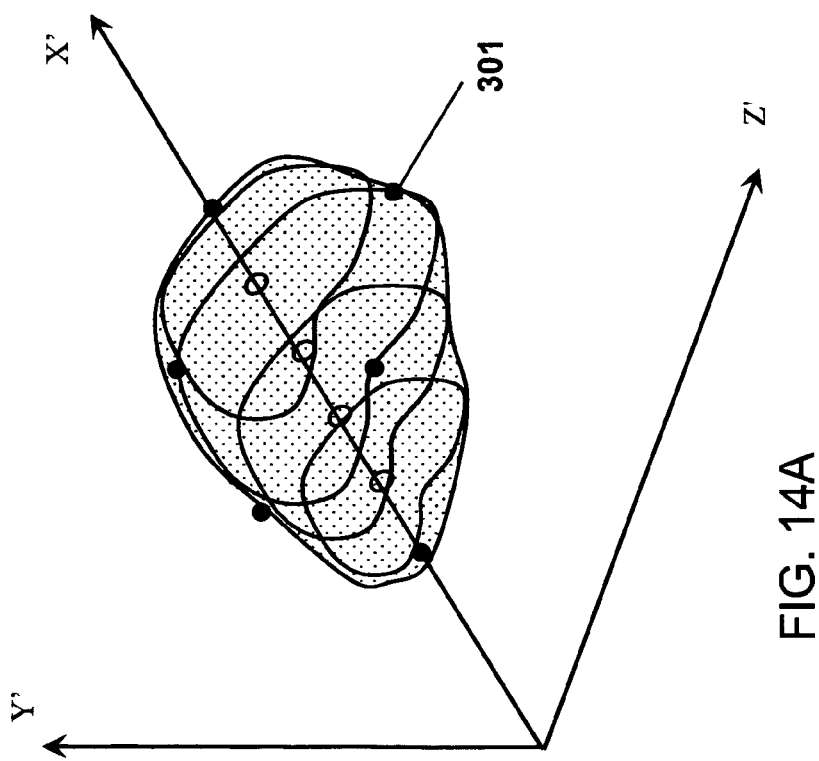
FIG. 14A is a simplified schematic showing a canonic model with pre-selected fitting points, according to an embodiment of the present invention.

FIG. 14A illustrates a canonic model of a prostate, which model represents the three-dimensional shape of one typical type of prostate. The system comprises a plurality of such models in the memory or data storage of controller 112, each model optionally being a 3D surface-rendered model of a prostate and each representing one of the typical prostate sizes and shapes. These models are stored in the system memory in an arbitrary coordinate system X'Y'Z'. Each canonic model further comprises a plurality of pre-selected landmark locations which can serve as 'anchors' or 'handles' for geometrical manipulation of the model, and which are useful in fitting a canonical model to a 3D model based on real-time observation of a patient. According to the Applicant's current practice, six such points are used, as illustrated in exemplary manner in FIG. 14B, but other numbers of points and other selections of points which are anatomically identifiable can be used.

Figure 14D:
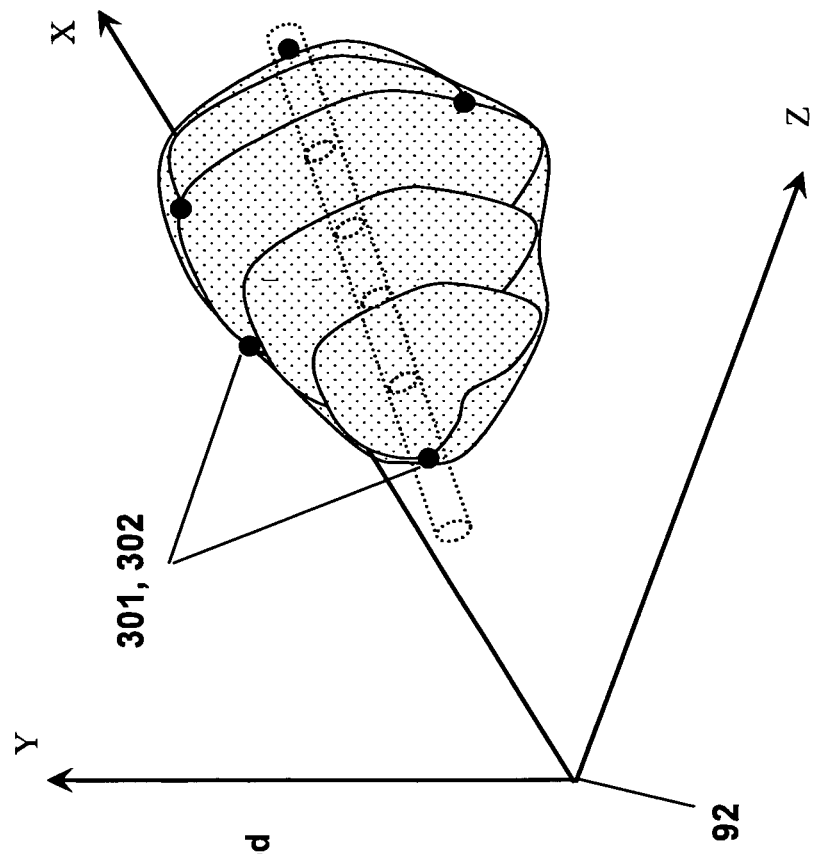
FIG. 14D is a continuation of FIG. 14C showing the canonical model fitted into six points by geometrical manipulations, according to an embodiment of the present invention.
Figure 14C:
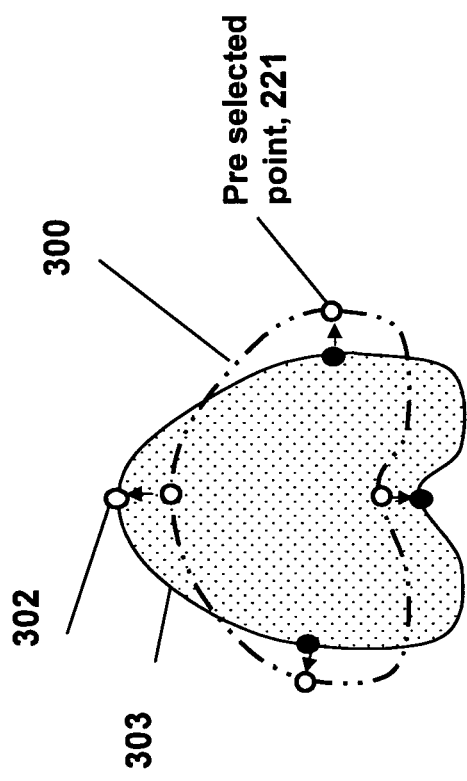
FIG. 14C is a simplified schematics illustrating geometrical fitting of a canonical model into marked points, to create 3D model of a patient's prostate, according to an embodiment of the present invention.

FIG. 14B shows six points marked on two ultrasound images presented on display 114. The marked points are extremities seen on a transverse cross section and on a longitudinal cross section. The spatial locations of each of the six points is detected and recorded as explained above. FIG. 14C shows how a user-selected canonical model may be 'fit' to a real-time model of a patient's prostate by stretching, squeezing, or otherwise graphically manipulating the model until the marked points of the model align with marked points on the real-time model (and/or on real-time 2D images of the organ). FIG. 14D shows how graphically adapting the canonic model to the real-time model causes the canonic model to be expressed in the XYZ coordinate system which is expressive of the real-time location information. This makes the details of the canonic model available to the real-time operation after some simple graphical manipulations matching only six points between one model and the other.

This fitting of volumes having corresponding sets of pre-selected points is a standard technique, as explained for example in Spath H., "Fitting affine and orthogonal transformations between two sets of points.", Mathematical Communications, 9(2004), pp 27-34.

A method using six points is exemplary only; smaller or larger numbers of marked points may serve for fitting the canonic model onto a set of marked points in order to create a 3D model that resembles the patient prostate. Controller 112 may have access to a data base containing a plurality of models of the prostate, enabling a physician to select a model that most closely approximates the prostate form that he observes, e.g. by selecting a model with similar proportions as measured by relative distances between specific marked points.

It is noted that the 'Fast 3D method' presented above for creating a 3D model, based on a limited number of real-time data points and a canonic model, can be used to model any organ. As elsewhere in this disclosure, references to the prostate are exemplary and not limiting.

Attention is now drawn to FIGS. 15A-15J, which are simplified schematics presenting methods for aligning two 3D models that were created at different times and at different positions of the patient. These methods can be used in the context of procedures disclosed herein for diagnosing and treating an organ such as a prostate, according to embodiments of the present invention.

Figure 15A:
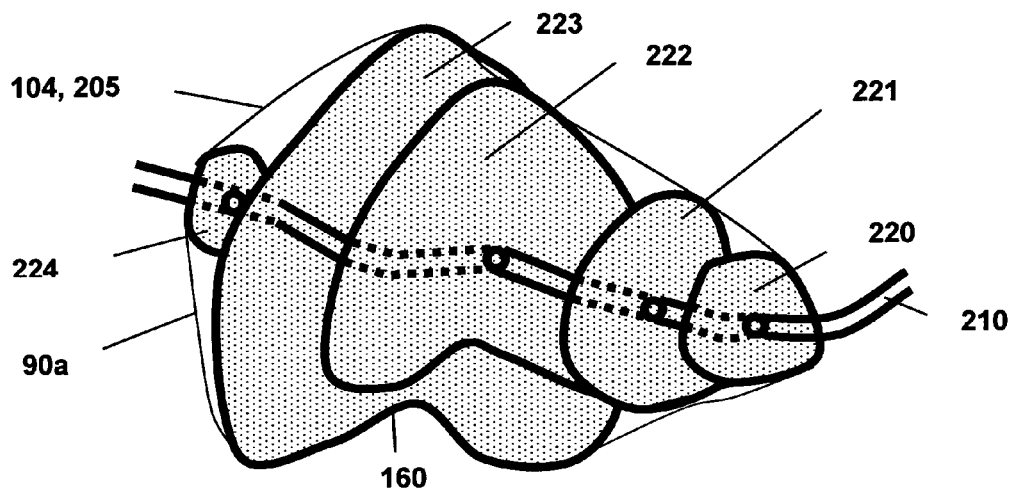
FIGS. 15A-15D are simplified schematics showing diagnostic-phase activities, according to embodiments of the present invention.

FIGS. 15A-15D present diagnostic-phase activities. FIG. 15A presents an organ 104 such as a prostate 205 as imaged by a clinical imaging modality 106a which may be, for example, an ultrasound system. Prostate 205, traversed by a prostatic urethra 210, is shown as imaged in "slices", as is standard practice in ultrasound and other forms of prostatic imaging. Slices 220, 221, 222, 223 and 224 are shown, together with their contours 160. Using well-known algorithmic methods including, for example, interpolation and projection, it is possible to construct a three-dimensional model 90a of organ 104 and its environment, based on a set of 'slice' such as images 220, 221, 222, 223 and 224 shown in FIG. 15A. Such images are typically taken at known and regular intervals, such as every 5 mm for example. Three-dimensional model 90a so produced constitutes a representation of organ 104 in a virtual three-dimensional space defined by a Cartesian coordinate system 92a or other coordinate system.

Figure 15B:
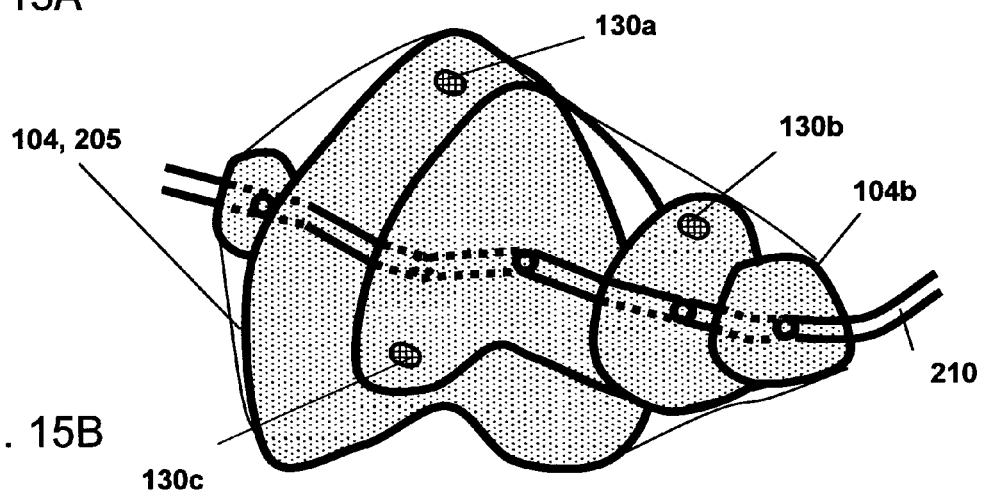

FIG. 15B shows fiducial markers 130, marked 130a, 130b, and 130c, inserted within organ 104.

Figure 15C:
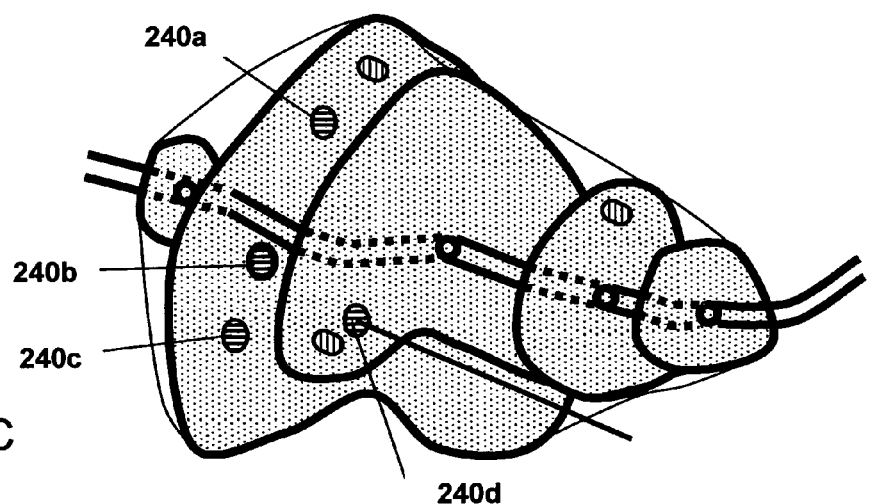

FIG. 15C shows the taking of a plurality of biopsy tissue samples from locations 240a, 240b, 240c, 240d etc., using one or more biopsy probes 145. An embodiment of the invention comprises taking of samples from a plurality of sites well distributed throughout organ 104.

Fiducial position markers 130 are designed to be visible under clinical imaging modalities 106a and 106b, enabling recording positions of sources of each biopsy sample taken. Positions may be identified with respect to positions of physiological landmarks, with respect to positions of markers 130, and/or with respect to a general coordinate system 92a of model 90a, within which fiducial markers 130 have known positions.

Fiducial markers 130 may be permanent or semi-permanent markers inserted into the body for purpose of guiding therapy and then left in the body at the conclusion of the therapy. For example, metal capsules may be used, such as the gold capsules supplied by Northwest Medical Physics Equipment under the trade name ACCULOC®. Alternatively, markers may be biodegradable. For example, a marker according to embodiments of the present invention may be a bubble of biocompatible gas such as $CO_2$ enclosed in a biodegradable membrane 131 such as a biocompatible biodegradable polymer, which enclosed bubble would be visible under ultrasound imaging. Such a biodegradable marker would disappear over time, as the materials of which it is composed are absorbed by surrounding tissues or carried away by the blood stream.

Figure 15D:
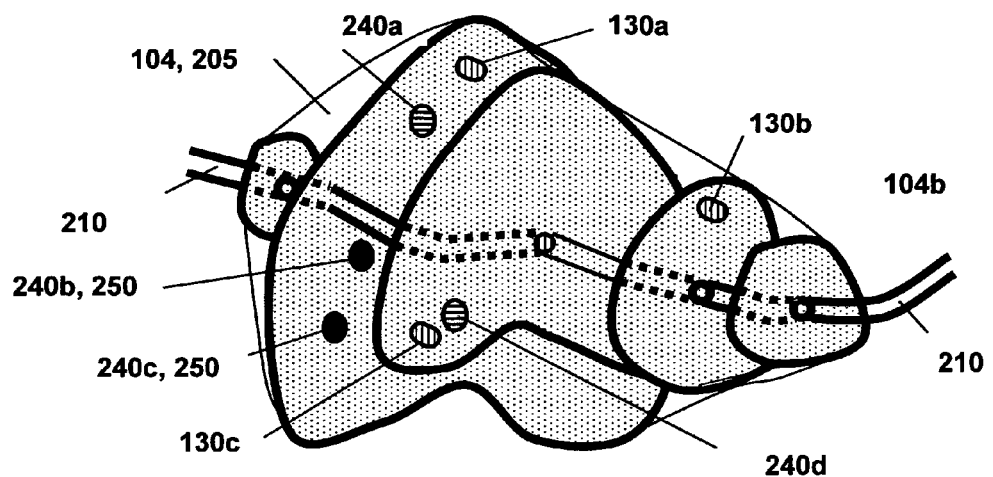

FIG. 15D presents results of procedures described at 78 and 79 of FIG. 2, wherein sites which are sources for biopsy samples found to contain pathological tissues are marked for treatment in model 90a. In exemplary FIG. 15D, biopsy sites 240b and 240c are labeled as treatment targets 250.

Figure 15E:
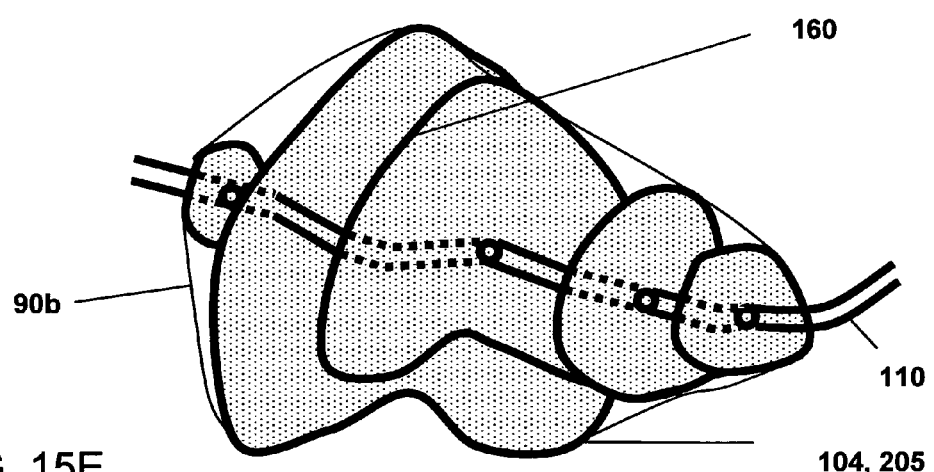
FIGS. 15E-15J are simplified schematics showing therapeutic-phase activities, according to an embodiment of the present invention.

FIGS. 15E-15J present treatment-phase activities corresponding to procedures 81, 82 and 84 of FIG. 3. Treatment-phase activity may take place hours or days after diagnostic phase activities. Treatment-phase activity comprises using imaging modalities 106b to create a set of second images 89b of target organ 104, as well as their contours 160 as shown in FIG. 15E and described at 81 in FIG. 3. Procedures 81 of treatment-phase activity are similar to procedures 71 and 72 of FIG. 2 of diagnostic phase activity. In both cases imaging modalities 106 are used to create a set of images 89 from which a 3-D model 90 is constructed. As noted above, equipment used for diagnostic and for treatment phase activities may be same equipment, similar but separate equipment, or may be different equipment entirely. In particular it is noted that imaging modalities, processors, and algorithms for imaging and for creating three-dimensional models during diagnostic phase and during treatment phase may be identical or may be widely different.

Figure 15F:
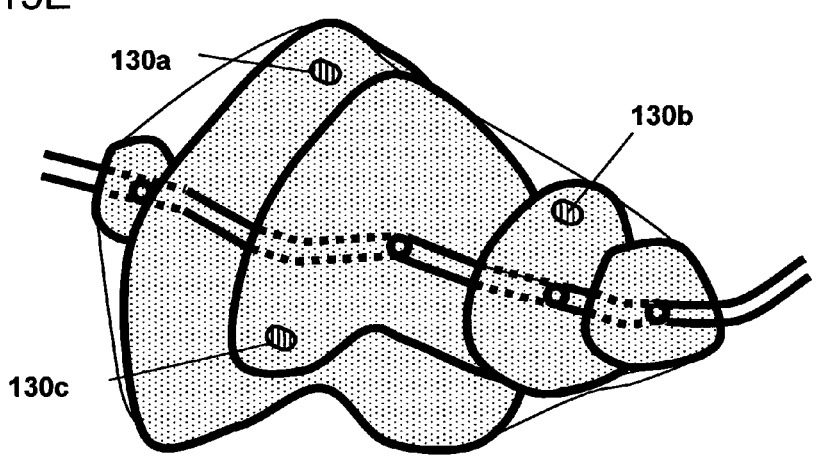

If fiducial markers 130 are implanted during diagnostic phase activity, those markers are identified and their locations noted, as shown in FIG. 15F as 130a, 130b, and 130c. Other objects introduced into the vicinity of organ 104 during diagnostic phase activity (e.g. a urethral straightener discussed below), may be re-introduced during treatment-phase activity, and positions of these too will be noted. Additionally, physiological landmarks may be identified algorithmically and/or these and markers 130 may be identified by a user through interface 113b.

Figure 15G:
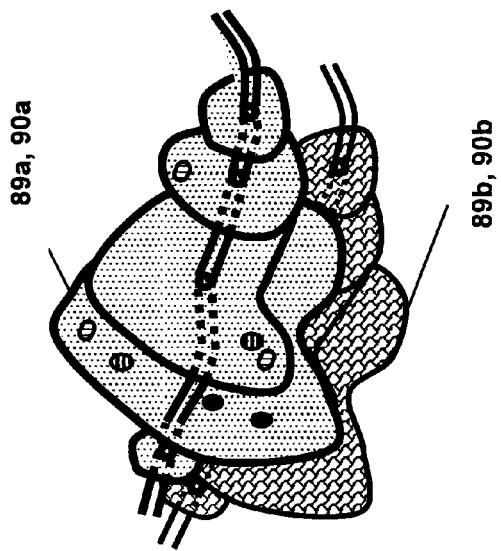
Figure 15H:
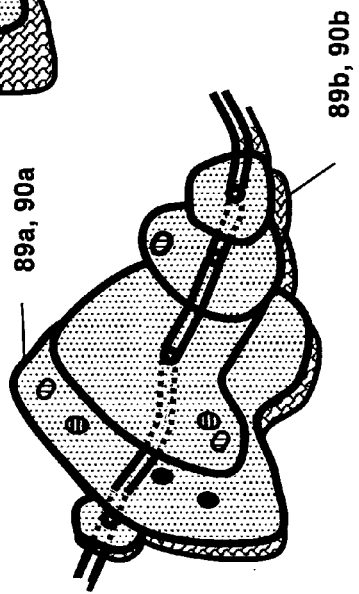

FIGS. 15G and 15H present phases of a process by which first and second images are related to each other.

In some embodiments, algorithmic procedures may be used to create first three-dimensional model 90a based on first images 89a, to create second three-dimensional model 90b based on second images 89b, and to relate first and second three dimensional models to each other in a common coordinate system 90c. Same objects (e.g. images of the entire prostate, images of features of the prostate such as lobes, urethral entrance and exit, implanted fiducial markers, etc.) may be identified in both first and second images, and their relative positions in those images used to deduce a systematic positional relationships between the images or between the models.

In some embodiments, user intervention may be used to facilitate this process. For example, a surgeon or other technician may be presented with displays of first and second images, and asked to identify physiological landmarks and/or fiducial markers in both images, thereby facilitating relating of first and second images and/or first and second 3-D models.

In some embodiments, a surgeon or technician may be enabled or instructed to manipulate imaging equipment such as ultrasound probes or other imaging modalities, so as to better align first and second images.

In some embodiments, graphic manipulation tools may be provided to a surgeon or technician enabling to relate first and second images one to another by graphic manipulation.

Figure 15I:
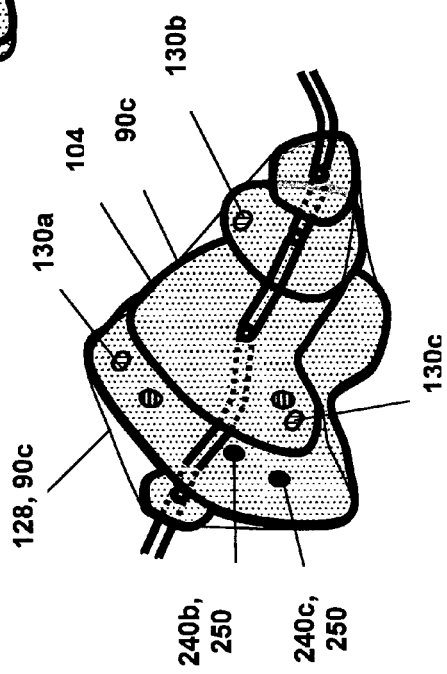

Any of the techniques mentioned in the preceding paragraphs and elsewhere herein may be used as indicated in FIGS. 15G and 15H, wherein first images 89a and second images 89b are aligned with each other; and/or first and second three-dimensional models 90a and 90b are mapped one to another. FIG. 15I presents a result of these processes, wherein a common image 128 is generated, either by graphic manipulation of a first image 89a combined with a second image 89b, or by generation of combined image 128 directly from a combined three-dimensional model 90c which comprises information from first model 90a and from second model 90b mapped into a common model 90c having a (Cartesian or other) coordinate system 92c with a known relationship to coordinate systems 92a and 92b.

In FIG. 15I, diagnostic information provided at 79 of FIG. 2 and shown at 240b and 240d of FIG. 15D is combined with real-time positional information provided at 81 of FIG. 3 and shown in FIGS. 15E and 15F. Thus, common model 90c can comprise, and common image 128 can show, both diagnostic and real-time information. Common image 128 can show an organ 104 as positioned within a patient on an operating table ready for a surgical intervention, can show positions of treatment probes or other surgical tools used during the intervention, and can also graphically show locations of sites determined during diagnostic phase activities to be targets of the intervention. A surgeon is thus provided with a graphic presentation of a virtual space in which his patient, his tools, and his surgical targets are together visible.

Figure 15J:
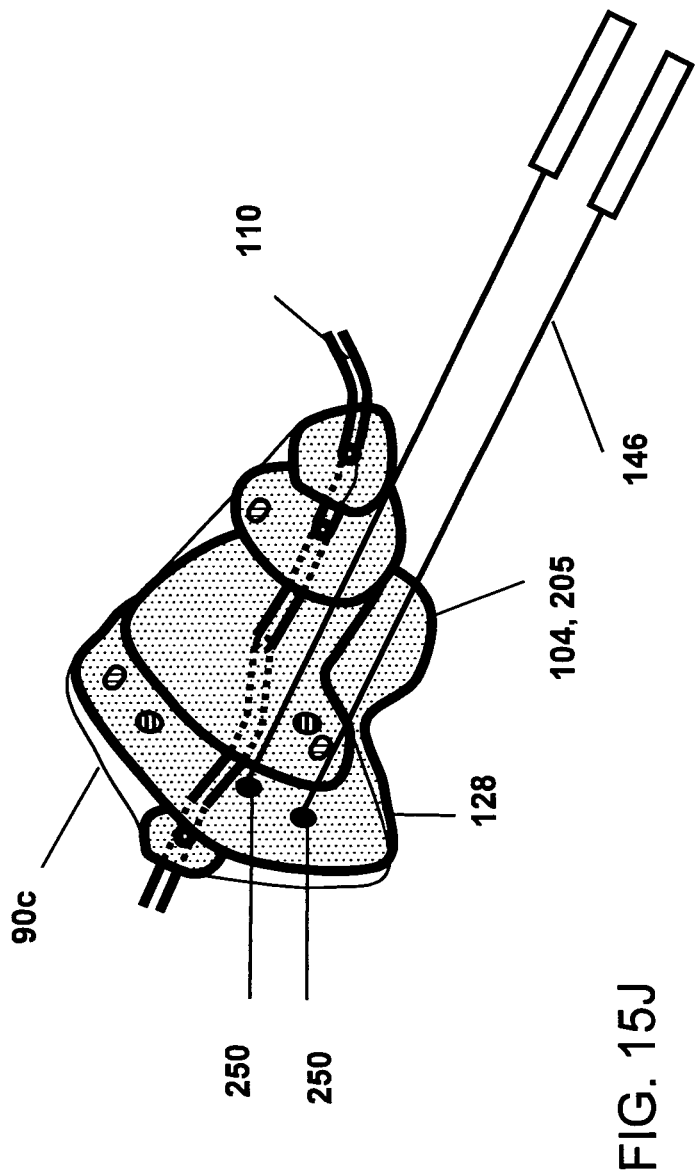

FIG. 15J portrays a surgical intervention in progress, with intervention probes 146 and target loci 250 both visible on common image 128.

In additional embodiments, combined information from models 90a and 90b are used to algorithmically direct intervention tools 146 towards surgical targets 250 under partial or complete algorithmic control. Relevant information is provided by control module 112b to servomotor controller 115b, which commands servomotor 119b and receives feedback from position sensor 117b, as discussed hereinabove. Position sensor 117b may be directly connected to treatment tool 146, or may alternatively be a remote sensor such as an ultrasound system and algorithmic detection system operable to detect position of tool 146 based on ultrasound images.

It is noted that use of fiducial markers 130 is optional. Such markers are a convenience in that they present easily visible positional signposts which facilitate aligning of first and second images and/or which facilitate relating a three-dimensional coordinate system of diagnostic 3-D model 90a based on first images with treatment 3-D model 90b based on second images. Procedures for relating first and second images may however be accomplished without requiring use of fiducial markers: physiological landmarks may be used instead to relate first images to second images. In the case of a prostate, for example, size and relative positions of prostate lobes, positions of major portions of the prostate mass, positions of entrance of the urethral passageway into the prostate and its exit therefrom, and similar objects may be used as landmarks, visible and identifiable in both first and second images, to align first and second images and/or first and second 3-D models. User-supplied information, such as user supplied identification of such landmarks on a raw ultrasound image or other image, may be used to facilitate this process.

The system here presented enables to direct tools toward targets. Various options for guiding tools toward targets are contemplated. These include automated techniques, such as automated guidance based on directional information derived from comparison of recorded locations of targets in a first coordinate system 92a to an observed or detected position of a treatment tool in second images 89b, graphical techniques such as presenting recorded images of target locations combined with real-time images of tool positions in a combined graphic image 128 constructed using information deriving from both recorded diagnostic phase sources and real-time treatment phase sources, and other forms of assistance which may be provided to a surgeon, such as verbal or graphical instructions on how to orient an imaging modality (such as an ultrasound probe) to produce real-time images easily comparable to recorded images, verbal or graphical instructions on how to orient a stereotactic probe guide or other tool delivery system, and verbal or graphical instructions showing when to insert a probe, what direction to point it in, and how far to advance it.

It is to be noted that (barring dramatic changes) mapping three-dimensional model 90A to three-dimensional model 90b enables to combine information from these models even when the treated organ has moved or changed shape in the interval between diagnostic activity and treatment activity, and even if the first and second images are created by imaging probes which are differently placed or differently used between the two phases of activity, and even if entirely different imaging modalities are used during the different phases of activity.

This being said, it is also noted that simplicity of equipment and convenience of procedures may be achieved by enhancing similarity between first and second images, and various embodiments of the invention are provided for this purpose. In general, some embodiments comprise means for similarly constraining the form or position of a target organ both during diagnostic phase activities and during treatment phase activities, thereby enhancing similarity between first and second images and thereby facilitating relating of first and second images to each other and/or relating first and second 3-D models to each other.

For example, uterine manipulators, previously used for stabilizing the uterus during treatment of nearby tissues, may be used for this purpose. A uterine manipulator called "LUMIN" marketed at www.utahmed.com/lumin.htm could be used to maintain similarity between diagnostic phase and therapy phase images, e.g. during diagnosis and later treatment of uterine fibroids.

An additional example of organ constraint in an embodiment of the present invention is provided in FIGS. 16A, 16B, which are simplified schematics of a urethral straightener positioned within a prostate, according to an embodiment of the present invention.

U.S. patent application Ser. No. 10/517,768 is incorporated herein by reference. That application teaches a urethral catheter with a straight section (or section with a known geometric form) which may be inserted into a prostatic urethra prior to imaging and/or treating a prostate. Such a catheter is referred to as a "urethral straightener" herein. The urethral straightener may have a section which is permanently straight (or with some other well-understood geometric form, such as a section of a circle with known diameter), or alternatively may be designed to be flexible when inserted, but to become stiff and of straight (or other known) form once inserted, e.g. through inflation of the catheter.

Use of such a urethral straightener is contemplated in some embodiments of the present invention. In particular, it is advantageous to insert a urethral straightener into a prostatic portion of a urethra prior to taking of first (diagnostic phase) images as shown in FIG. 15A, and again prior to creating second (treatment phase) images as shown in FIG. 15E. Use of a straightener during taking of both first and second images greatly increases similarities between the images and facilitates comparison of images and mapping of 3-D models one to another. Additionally, use of such a urethral straighten enhances stiffness of the prostate, reducing 'noise' which would otherwise be introduced by random changes in prostate shape and position induced by gravity and by other influences, such as TRUS pressures on the organ. It is noted that a urethral straightener can be provided with a sensor as described above for use with a urethral catheter, thereby combining straightening functionality and sensor functionality in a common tool.

The inserted urethral straightener may be a rigid rod, preferably straight, or may have a flexible structure facilitating insertion, with capacity to be caused to straighten (e.g. by inflation under pressure) subsequent to insertion, as taught in U.S. patent application Ser. No. 10/517,768.

FIG. 16A demonstrates use of an organ constraining device 255 exemplified as a urethral straightener 260, shown as inserted into the prostatic urethra 210 of a prostate 205, according to an embodiment of the present invention. Use of a urethral straightener inserted within the prostatic urethra is exemplary of "position standardization" of an organ or portion of an organ, and is exemplary of a general class of physical apparatus for constraining an organ, in a reproducible manner, to a predetermined form or position or condition or orientation. An organ constraining device 255, such as a urethral straightener 260, is optionally used during creation of both first images 89a and second images 89b, thereby facilitating comparisons of the two and facilitating relating of first images to second images.

FIG. 16B discloses another method of using the prostatic urethra as a landmark for enhanced mapping technique of the prostate, according to an embodiment of the present invention. The urethra, 210, can be easily identified under imaging. Moreover, the urethra entrance to the bladder neck, 211, and the prostate-urethra end at the apex, 212, are two anatomical sites that can be identified and marked on the imaging screen during both a first session and a second session, their positions being recorded each time. Two or more such landmarks create as an imaginary line with clear relationship to the organ anatomy. Using this spatially recognized imaginary line, (213 in the figure) to align images or models from a first session with images or models from a second session greatly simplifies the use of other analytical tools and alignment algorithms.

According some embodiments, a first step for alignment between two models is to translate the first model to a position at which its imaginary fine, 213, fits the spatial location of the imaginary line, 213, of the second model. A second step is rotate one of the models around line 213, finding the rotation angle at which the two models are best aligned. That angle is angle θ as discussed below.

Figure 17B:
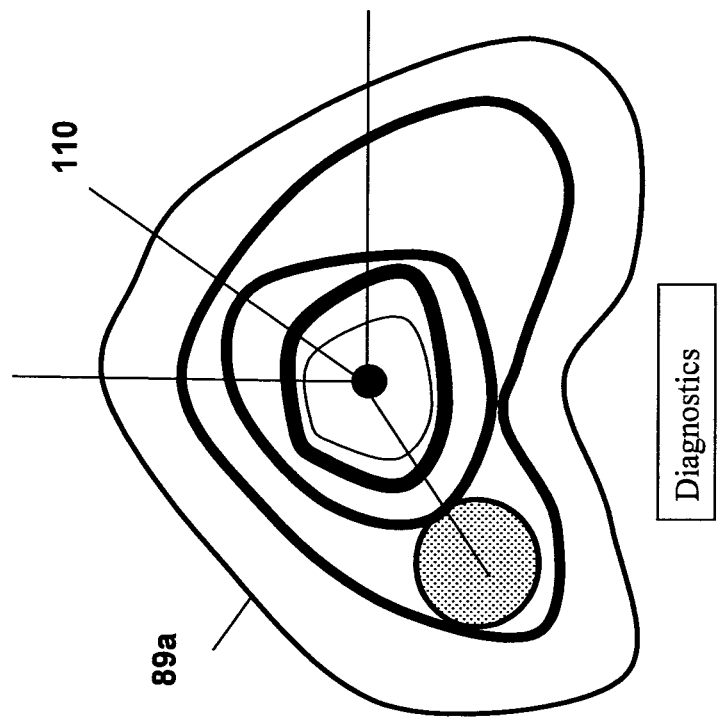
FIGS. 17A and 17B are a simplified schematic showing angle of rotation around an axis formed by two anatomical landmarks in a prostate and prostate base, and around a straightener in a urethra and between these landmarks, according to an embodiment of the present invention.
Figure 17A:
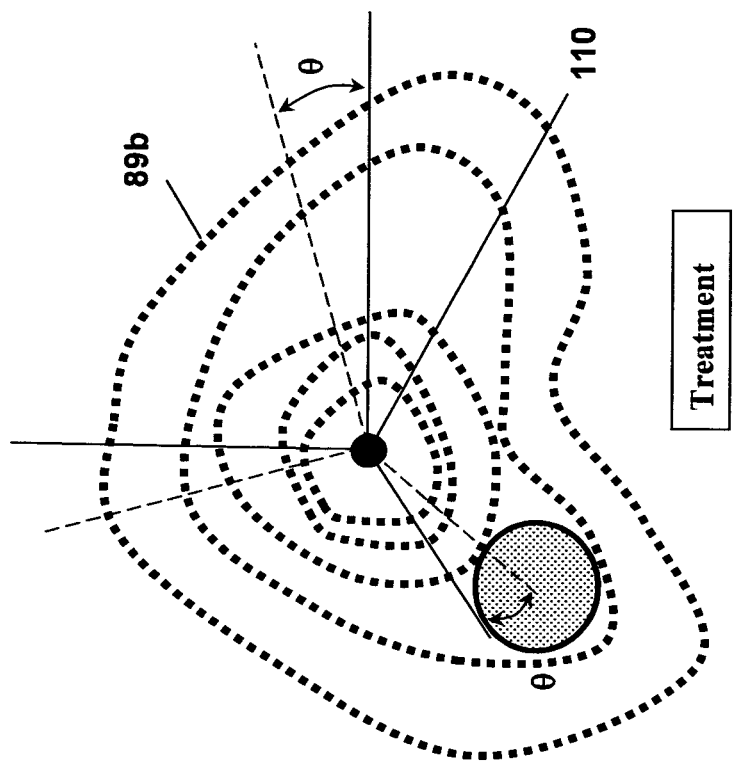

Attention is now drawn to FIGS. 17A and 17B, which are simplified schematics demonstrating comparison of first and second images created while using a urethral straightener, according to an embodiment of the present invention. Not only does use of a straightener simplify processing when comparing images by inducing a elements of uniformity between the first and second images, but also, with the prostatic urethra straightened, first and second images and/or first and second models may be easily aligned with the straight prostatic urethra as common longitudinal axis. FIGS. 17A and 17B presents comparison of a composite first image 89a with a composite second image 89b, the images being taken as if along the straightened urethra 110, shown centered in each image. Similarities in the images are immediately apparent to the eye. An angle of rotation θ of image 89b with respect to image 89a is easily determined by eye, by graphical rotation of one of the images around the urethra as axis, or by algorithmic comparison (e.g. by comparing positions of the largest imaged prostate lobe, the one having its border furthest from the prostate axis).

It is again noted that contemplated embodiments may include facilities for manipulating the imaging equipment to enhance similarity of first and second images (e.g. by rotating an ultrasound probe to line up images 89a and 89b as shown in FIGS. 17A and 17B, or optionally by showing the images superimposed one on another and in different colors). Contemplated embodiments may also include facilities for graphically manipulating those images (i.e. manipulating the imaging presentation through a graphical user interface, rather than manipulating the imaging probe in a patient), and may also include algorithmic methods well known in the art for reducing dissimilarity between the images and recording the transformations required to do so. An additional optional embodiment comprises a device connectable to a urethral straightener on the one hand and to an imaging probe on the other hand, operable to standardize positioning of one with respect to the other during first and second imaging processes. Alternatively, position sensors mounted on a urethral straightener or position markers, such as echogenic markers visible on a urethral straightener under ultrasound imaging, can also provide position and orientation information facilitating comparison of first and second images and mapping between first and second models.

Additionally, some embodiments comprise means for adjusting a probe delivery apparatus as a function of detected differences between first and second images. Attention is drawn to FIGS. 18A-18C, which are samples of output of a simulator running an algorithm appropriate for detecting angle θ based on first and second image inputs shown in the Figures, the algorithm outputting instructions to a surgeon detailing how to position a stereotactic probe placement template so that probe positioning information based on first images will be usable on a prostate positioned as shown in second images.

Figure 18A:
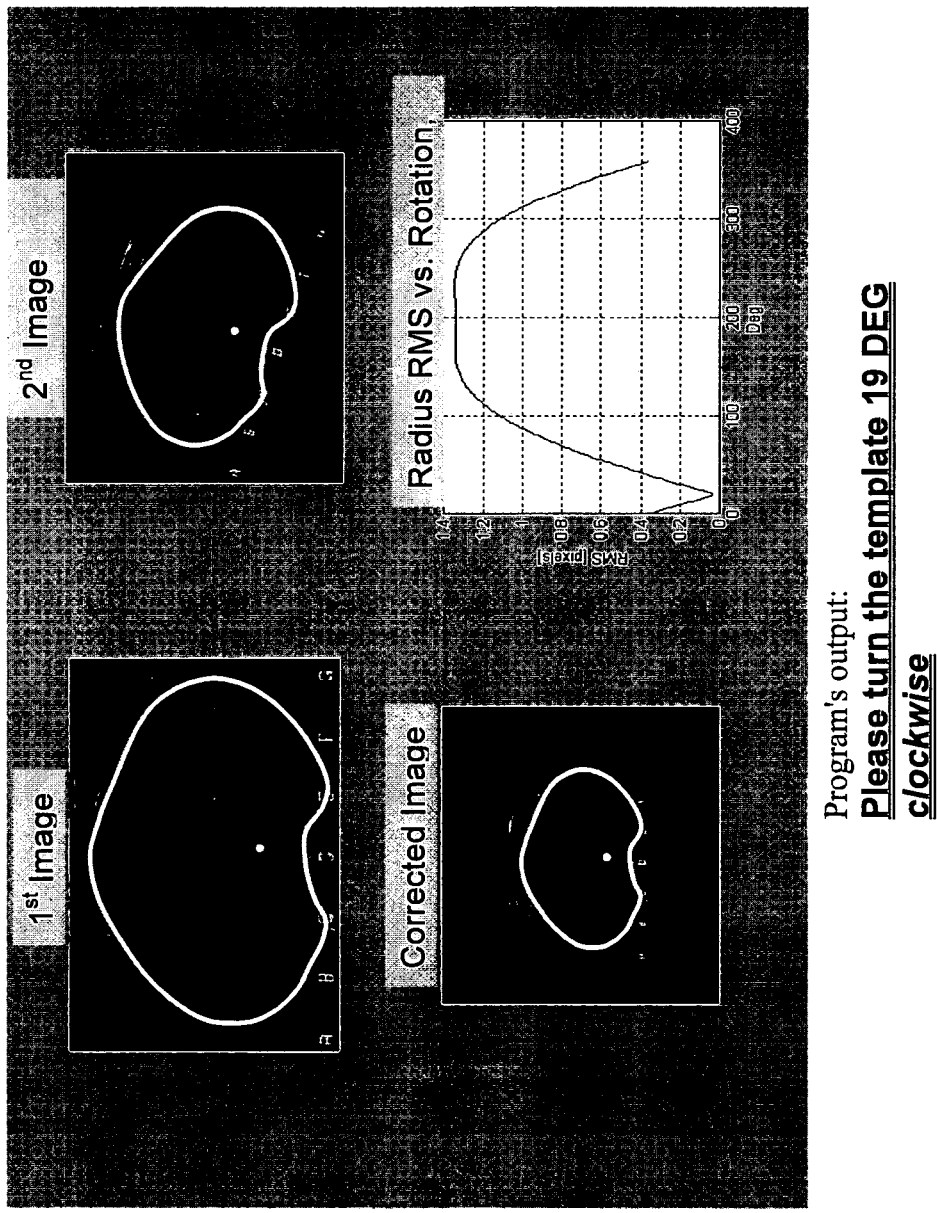
FIGS. 18A-18C are image samples of system output showing instructions for aligning angle of rotation between two 3D models, according to an embodiment of the present invention.
Figure 18B:
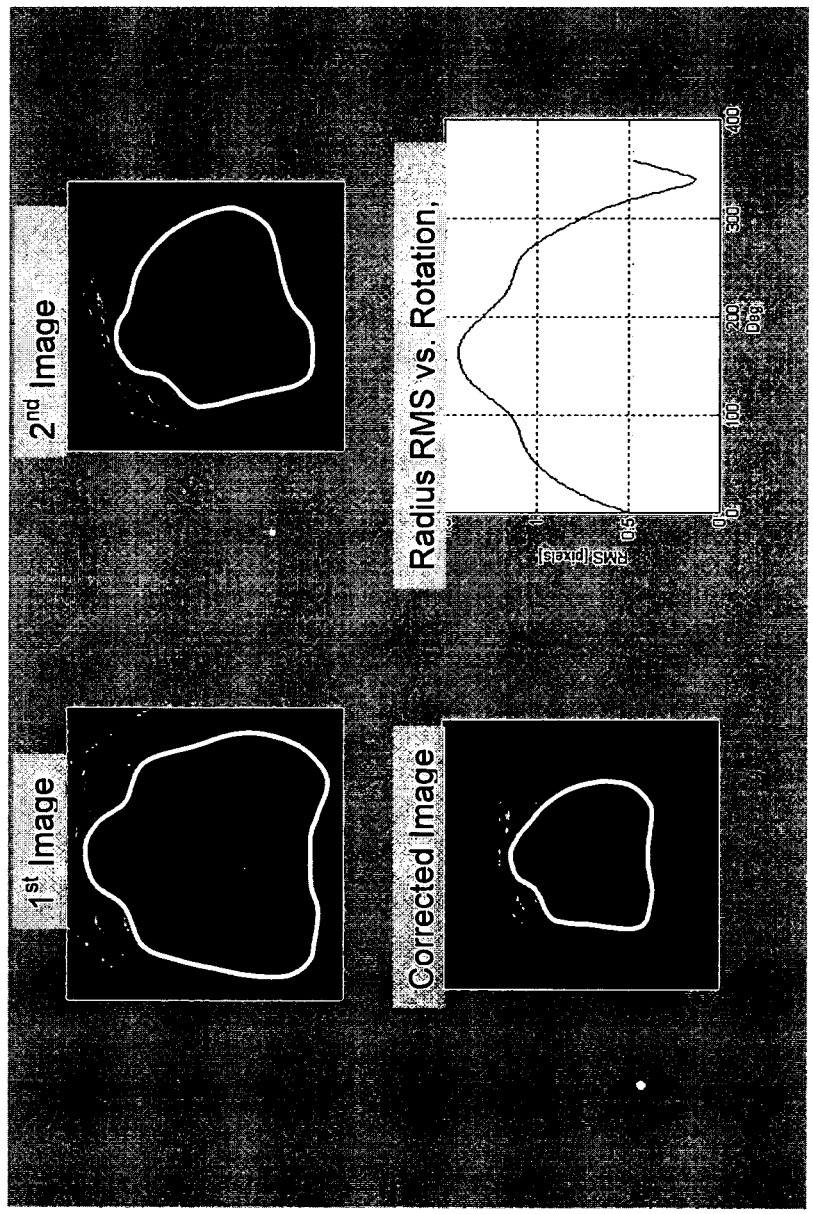
Figure 18C:
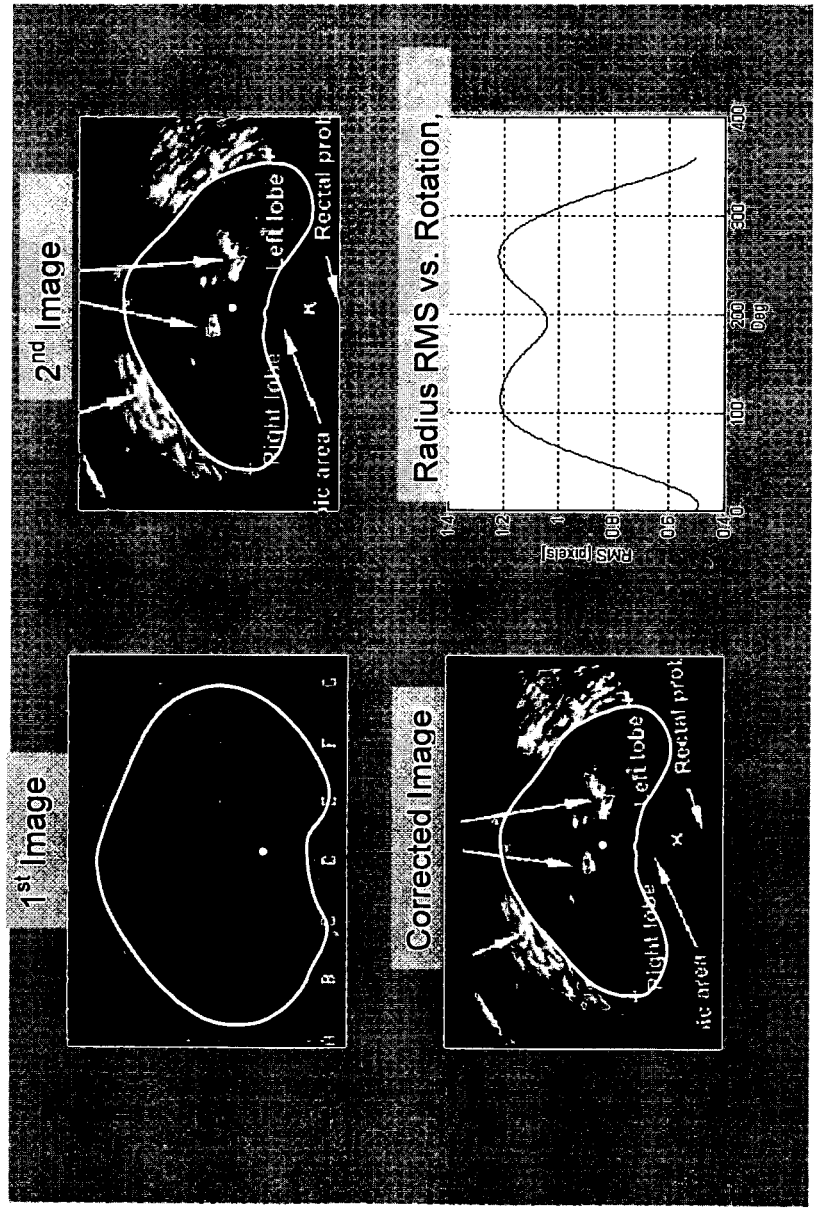

The exemplary algorithm used to produce FIG. 18A-18C may be described as follows:

First and second sets of first and second "slice" images of a prostate containing a urethral straightener (and optionally containing fiducial markers) are presented to a user who uses a graphical interface to mark prostate borders and urethral position on the presented images. (On the actual screen, the border marking is in a distinct color such as red.)

Radial distances (from central urethra to prostate border) are measured or estimated at a plurality of radial angles around each of corresponding first and second slice images, and a similarity score for a given 'rotation' of one set of images with respect to the other is calculated as square root of the sum of the squares of the differences between each first image radial measurement and a corresponding second image radial measurement. Thus for a given rotational orientation of the set of first images with respect to the set of second images, a general RMS score may be calculated.

The process is then repeated for a plurality of rotational variants of the set of first images with respect to the set of second images. Thus for example if 100 rotational variants are to be tested, an RMS score may be calculated for zero rotation of first with respect to second images, then either first or second images may be 'rotated' (in virtual space) by e.g 1/100 of 2π and another RMS score calculated. After 100 such 'rotations', the positional rotation yielding the lowest RMS score is considered to be a "match", and appropriate instructions are provided to a user or to a probe placement system. (In the case of the embodiment shown in FIGS. 18A-18C, instructions for appropriate rotation of a probe placement template are displayed by the system.)

The algorithm explanation of the preceding paragraphs has been simplified to present the principle behind the process. Actual calculation methods may be modified as appropriate for efficient calculation, using techniques well known in the art. For example, it is of course unnecessary to actually rotate the images, and unnecessary to measure radial distances on the images more than once. Once sets of radial measurements having been made, RMS scores may be calculated by calculating differences between a set of first image radial measurements starting at angle 0° and going around the first image, with a set of second image radial measurements starting at angle (0° plus an increasing factor) and going around the second image. Similarly, comparison scores for all possible rotations need not be calculated since the range of possible actual rotations of the prostate images (between first image taking and second image taking) will be subject to practical limitations.

It is further noted that although the calculation here described may be implemented on sets of 'slice' images 89*a* and 89*b*, alternatively three dimensional models 90*a* and 90*b* may be constructed using commercially available model construction software or other methods well known in the art (interpolation etc.), and then new sets of derived slice images derived from the 3D models may be created, again using well-known methods, and those derived first and second slice images may be compared. Alternatively, appropriate measurements of distances between urethra and prostate border may be derived directly from the models. Working from models, it is possible to seek to match first and second models in several dimensions, again using a best-fit (minimal RMS difference score) as the models are compared, to detect a best fit over possible rotations in several dimensions. Such methods are particularly important if no urethral straightener is used, since the urethral straightener can constrain orientation of the prostate around the urethral axis and/or can report the actual direction of a urethra within which a urethral straightener has been inserted.

It is further noted that first and second images may typically differ in that an imaging modality (such as an ultrasound probe) may be closer to the prostate during imaging one set of images than it is during imaging of a second set of images, and thereby produce a larger set of images. Integrating the radial measurements over the entire prostate for both first and second images (or models) will yield first and second integral values corresponding to an apparent prostate "volume" as shown in the image sets. The ratio of the apparent volume of the first images divided by the apparent volume of the second images represents the relative "enlargement" of one of the sets of images with respect to the other. This information may be used to normalize the two sets of images (or models) to a common apparent size, thereby facilitating calculations and facilitating the creating of composite image 128 if desired.

As used herein the term "about" refers to ±10%.

The terms "comprises", "comprising", "includes", "including", "having" and their conjugates mean "including but not limited to".

The term "consisting of means "including and limited to".

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

We claim:

1. A system for locating lesions in an organ, comprising:
A) a tracking system including an electromagnetic signal transmitter positionable near a patient and sensors configured to sense an electromagnetic signal emitted by the electromagnetic signal transmitter, the sensors including at least one first sensor attached to a body of the patient and at least one second sensor, wherein the tracking system is configured to report the sensors' position within a fixed three-dimensional (3D) coordinate system relative to the position of the electromagnetic signal transmitter in real time; and
B) a controller, including at least one processor, a 3D modelling module, and a display;
the at least one processor configured to:
receive image data including image pixels from an imaging modality including an imaging probe, the imaging probe having a fixed spatial relationship with the at least one second sensor;
use position data of the at least one second sensor to register image pixels of images received from the imaging modality into the 3D coordinate system;

use said 3D modelling module to create a 3D virtual model of an organ of the patient from a series of first images received during a first phase activity from the imaging modality; and register a landmark of the organ on the 3D virtual model of the organ; and the at least one processor is further configured to in real time:

employ real-time position data received from the at least one first sensor to compensate for body movements of the patient between the first phase activity and a second phase activity, thereby relating to a second image of the organ obtained during the second phase activity a body-movements-compensated position;

identify a landmark of the organ in the second image; and align the landmark in the second image with the landmark in the 3D virtual model to map the second image onto the 3D virtual model and to display on the display a composed image including the second image mapped onto the 3D virtual model.

2. The system of claim 1 wherein the organ is a prostate and the second image is obtained by an ultrasound transducer.

3. The system of claim 2 wherein the landmark is at least one of prostate borders, a prostatic urethra, an urethra entrance to a bladder neck, a prostate urethra end at an apex of the prostate, or seminal vesicles near the prostate.

4. The system of claim 2 wherein the at least one second sensor is attached to the imaging probe.

5. The system of claim 1 wherein the first image and the second image are obtained from different imaging modalities.

6. The system of claim 1 wherein the 3D virtual model includes image pixels received from the imaging modality.

7. The system of claim 1 wherein the second image is a graphical representation of a second 3D virtual model created during the second phase activity.

8. The system of claim 1 wherein the identification of the landmark of the organ in the second image is performed algorithmically.

9. A method of locating lesions in an organ of a live patient, the method comprising:

receiving image data including image pixels of the organ from a first imaging modality including a first imaging probe;

using a tracking system including an electromagnetic signal transmitter positionable near the patient and at least one first sensor configured to sense the electromagnetic signal, the at least one first sensor having a fixed spatial relationship with the first imaging probe of the first imaging modality;

receiving real-time position information of the first imaging probe;

calculating a position of each image pixel thereby registering the image pixels in a three-dimensional (3D) coordinate system;

creating a 3D virtual model of the organ from a series of images obtained during a first phase activity from the first imaging modality;

virtually marking at least one landmark of the organ on the 3D virtual model;

after the first phase activity, obtaining at least one second image from image data including image pixels received during a second phase activity from a second imaging modality including a second imaging probe, the second imaging probe having a fixed spatial relationship with the at least one first sensor of the tracking system;

using at least one second sensor of the tracking system attached to the body of the patient, compensating for patient's body movements during a time interval between the first phase activity and the second phase activity, thereby relating to the at least one second image a body-movements-compensated position;

identifying at least one landmark of the organ on the second image;

aligning the identified at least one landmark on the second image with the marked landmark on the 3D virtual model;

mapping the second image onto the 3D virtual model; and displaying, in real-time with the receiving of the image data from the second imaging modality, a combined image comprising the at least one second image mapped onto the 3D virtual model of the organ.

10. The method of claim 9 wherein the first imaging modality and the second imaging modality are the same.

11. The method of claim 9 wherein identifying at least one landmark of the organ on the second image includes user assistance.

12. The method of claim 9 wherein the organ is a prostate and the at least one landmark is an anatomical landmark including at least one of prostate borders, a prostatic urethra, an urethra entrance to a bladder neck, a prostate-urethra end at an apex of the prostate, or seminal vesicles near the prostate.

13. The method of claim 9 wherein the first imaging modality includes an MRI system.

14. The method of claim 9 wherein the second imaging modality includes an ultrasound transducer.

15. The method of claim 9 wherein the 3D virtual model includes image pixels received from the first imaging modality.

16. The method of claim 9 wherein the at least one second image is a graphical representation of a second 3D virtual model created during the second phase activity.

* * * * *